US009265674B2

(12) United States Patent
Hancock-Cooke et al.

(10) Patent No.: US 9,265,674 B2
(45) Date of Patent: Feb. 23, 2016

(54) ABSORBENT ARTICLE HAVING A FASTENING SYSTEM WITH LOW STIFFNESS

(71) Applicant: Kimberly-Clark Worldwide, Inc., Neenah, WI (US)

(72) Inventors: Catherine Hancock-Cooke, Neenah, WI (US); David F. Bishop, Appleton, WI (US); Jeffrey DeBroux, Appleton, WI (US); David J. Enz, Neenah, WI (US); Alanna Haessler, Appleton, WI (US); Robert Lee Popp, Greenville, WI (US); Sara Jane Wille Stabelfeldt, Appleton, WI (US); Wendy Lynn VanDyke, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 101 days.

(21) Appl. No.: 13/953,396

(22) Filed: Jul. 29, 2013

(65) Prior Publication Data

US 2015/0032077 A1 Jan. 29, 2015

(51) Int. Cl.
*A61F 13/15* (2006.01)
*A61F 13/62* (2006.01)
*A61F 13/56* (2006.01)

(52) U.S. Cl.
CPC .......... *A61F 13/625* (2013.01); *A61F 13/15747* (2013.01); *A61F 13/15756* (2013.01);
(Continued)

(58) Field of Classification Search
CPC . A61F 13/5633; A61F 13/625; A61F 13/627; A61F 13/62; A61F 13/5622; A61F 13/5644; A61F 13/5638; A61F 13/15747

USPC ............................................................ 604/391
See application file for complete search history.

(56) References Cited

U.S. PATENT DOCUMENTS

| 4,010,754 A | 3/1977 | Pieniak |
| 4,050,462 A | 9/1977 | Woon et al. |

(Continued)

FOREIGN PATENT DOCUMENTS

| EP | 0233704 | 7/1992 |
| EP | 0476992 | 7/1995 |

(Continued)

OTHER PUBLICATIONS

International Search Report and Written Opinion for PCT/IB2014/063095 dated Dec. 2, 2014; 13 pages.

*Primary Examiner* — Bradley Philips
(74) *Attorney, Agent, or Firm* — Armstrong Teasdale LLP

(57) ABSTRACT

An absorbent article is provided. The absorbent article includes a bodyside liner, an outer cover, and an absorbent core between the liner and the outer cover. The absorbent article further includes a pair of ears extending outward from the opposite sides of the absorbent article, and a fastening system having a primary fastening system and a secondary fastening system. The primary fastening system includes a primary first fastening component disposed on each of the pair of ears and a primary second fastening component disposed on the outer surface of the article. The secondary fastening system includes a secondary second fastening component on each of the pair of ears and a corresponding secondary first fastening component on the outer surface of the article. Each of the secondary first fastening components has a stiffness in the longitudinal direction of the article of less than 185 milligrams according to a Gurley Stiffness Test.

38 Claims, 23 Drawing Sheets

(52) U.S. Cl.
CPC ......... *A61F13/5633* (2013.01); *A61F 13/5638* (2013.01); *A61F 13/5644* (2013.01); *A61F 13/627* (2013.01)

(56) References Cited

U.S. PATENT DOCUMENTS

| | | | |
|---|---|---|---|
| 4,253,461 A | 3/1981 | Strickland et al. | |
| 4,500,316 A | 2/1985 | Damico | |
| 4,585,448 A | 4/1986 | Enloe | |
| 4,699,622 A | 10/1987 | Toussant et al. | |
| 4,753,650 A | 6/1988 | Williams | |
| 4,770,656 A | 9/1988 | Proxmire et al. | |
| 4,773,906 A | 9/1988 | Krushel | |
| 4,801,298 A | 1/1989 | Sorenson et al. | |
| 4,850,988 A | 7/1989 | Aledo et al. | |
| 4,850,992 A | 7/1989 | Amaral et al. | |
| 4,923,456 A | 5/1990 | Proxmire | |
| 4,936,840 A | 6/1990 | Proxmire | |
| 4,988,346 A | 1/1991 | Pfefferkorn | |
| 5,019,072 A | 5/1991 | Polski | |
| 5,069,678 A | 12/1991 | Yamamoto et al. | |
| 5,108,384 A | 4/1992 | Goulait | |
| 5,151,092 A | 9/1992 | Buell et al. | |
| 5,176,671 A | 1/1993 | Roessler et al. | |
| 5,242,436 A | 9/1993 | Weil et al. | |
| 5,325,569 A | 7/1994 | Goulait et al. | |
| 5,358,500 A | 10/1994 | Lavon et al. | |
| 5,368,585 A | 11/1994 | Dokken | |
| 5,370,634 A | 12/1994 | Ando et al. | |
| 5,383,871 A | 1/1995 | Carlin et al. | |
| 5,392,498 A | 2/1995 | Gouliait et al. | |
| 5,409,476 A | 4/1995 | Coates | |
| 5,593,401 A | 1/1997 | Sosalla et al. | |
| 5,603,794 A | 2/1997 | Thomas et al. | |
| 5,624,428 A | 4/1997 | Sauer | |
| 5,685,873 A | 11/1997 | Bruemmer | |
| 5,830,206 A | 11/1998 | Larsson | |
| 5,997,522 A | 12/1999 | Provost et al. | |
| 6,030,373 A | 2/2000 | VanGompel et al. | |
| 6,045,543 A | 4/2000 | Pozniak et al. | |
| 6,056,732 A | 5/2000 | Fujioka et al. | |
| 6,099,516 A | 8/2000 | Pozniak et al. | |
| 6,102,901 A | 8/2000 | Lord | |
| 6,142,983 A | 11/2000 | Suprise et al. | |
| 6,142,986 A | 11/2000 | Lord et al. | |
| 6,174,303 B1 | 1/2001 | Suprise et al. | |
| 6,287,287 B1 | 9/2001 | Elsberg | |
| 6,322,552 B1 | 11/2001 | Blenke et al. | |
| 6,371,951 B1 | 4/2002 | Koczab et al. | |
| 6,402,731 B1 | 6/2002 | Suprise et al. | |
| 6,406,466 B1 | 6/2002 | Pozniak et al. | |
| 6,551,294 B1 | 4/2003 | Elsberg et al. | |
| 6,554,816 B1 | 4/2003 | Olson | |
| 6,613,032 B2 | 9/2003 | Ronnberg et al. | |
| 6,890,630 B2 | 5/2005 | Franklin et al. | |
| 6,976,978 B2 | 12/2005 | Ruman et al. | |
| 7,122,024 B2 | 10/2006 | Nakajima et al. | |
| 7,150,732 B2 | 12/2006 | Yoshida et al. | |
| 7,252,658 B2 | 8/2007 | Sayama | |
| 7,344,525 B2 * | 3/2008 | Linker et al. ................... | 604/391 |
| 7,449,017 B2 | 11/2008 | Yoshida | |
| 7,455,665 B2 | 11/2008 | Wendelstorf et al. | |
| 7,534,481 B2 | 5/2009 | Seth et al. | |
| 7,578,813 B2 * | 8/2009 | Mitsui et al. ................... | 604/391 |
| 7,662,137 B2 | 2/2010 | Sayama et al. | |
| 8,118,801 B2 | 2/2012 | Macura et al. | |
| 8,353,891 B2 | 1/2013 | Hornung et al. | |
| 8,395,017 B2 | 3/2013 | Nakahata et al. | |
| 2002/0016581 A1 | 2/2002 | Kline et al. | |
| 2002/0058923 A1 | 5/2002 | Suprise et al. | |
| 2002/0095130 A1 | 7/2002 | Seitter et al. | |
| 2002/0095132 A1 | 7/2002 | Ashton et al. | |
| 2002/0123734 A1 | 9/2002 | Carlbark et al. | |
| 2002/0138059 A1 | 9/2002 | Van Gompel et al. | |
| 2002/0138064 A1 | 9/2002 | Datta et al. | |
| 2002/0169431 A1 | 11/2002 | Kline et al. | |
| 2002/0173768 A1 | 11/2002 | Elsberg et al. | |
| 2002/0174934 A1 | 11/2002 | Johnson et al. | |
| 2003/0044578 A1 | 3/2003 | Nissing | |
| 2003/0100880 A1 | 5/2003 | Magee et al. | |
| 2004/0129592 A1 | 7/2004 | Otsubo | |
| 2004/0158224 A1 | 8/2004 | Kline et al. | |
| 2004/0243091 A1 | 12/2004 | Mitsui et al. | |
| 2004/0261233 A1 | 12/2004 | Kingsford et al. | |
| 2005/0043700 A1 | 2/2005 | Otsubo et al. | |
| 2005/0143710 A1 | 6/2005 | Van Gompel et al. | |
| 2005/0148976 A1 | 7/2005 | Van Gompel et al. | |
| 2005/0148977 A1 | 7/2005 | Van Gompel et al. | |
| 2005/0148982 A1 | 7/2005 | VanGompel et al. | |
| 2005/0148985 A1 | 7/2005 | Bronk et al. | |
| 2005/0148986 A1 | 7/2005 | Collins et al. | |
| 2006/0004337 A1 | 1/2006 | Datta | |
| 2006/0069378 A1 | 3/2006 | Winkel et al. | |
| 2006/0069379 A1 | 3/2006 | Van Gompel et al. | |
| 2006/0293639 A1 | 12/2006 | Van Gompel et al. | |
| 2007/0093769 A1 | 4/2007 | Kline et al. | |
| 2007/0250026 A1 | 10/2007 | Venturino et al. | |
| 2008/0058753 A1 | 3/2008 | Dalal | |
| 2008/0114323 A1 | 5/2008 | Kline et al. | |
| 2008/0132863 A1 | 6/2008 | Waksmundzki et al. | |
| 2008/0172840 A1 | 7/2008 | Kacker et al. | |
| 2009/0076783 A1 | 3/2009 | Babusik et al. | |
| 2009/0299317 A1 | 12/2009 | Flannery | |
| 2009/0299318 A1 | 12/2009 | Faulks et al. | |
| 2009/0299322 A1 | 12/2009 | Faulks et al. | |
| 2009/0299323 A1 | 12/2009 | Schlinz et al. | |
| 2010/0234822 A1 * | 9/2010 | Back ........................ | 604/385.3 |
| 2011/0100526 A1 | 5/2011 | Umebayashi | |
| 2012/0157958 A1 | 6/2012 | Tenorio et al. | |
| 2013/0211361 A1 | 8/2013 | Anderson et al. | |
| 2014/0350507 A1 | 11/2014 | Pariseau et al. | |

FOREIGN PATENT DOCUMENTS

| | | |
|---|---|---|
| EP | 1600132 | 11/2005 |
| EP | 1688117 | 8/2006 |
| EP | 2335504 | 4/2013 |
| GB | 2033210 | 10/1979 |
| JP | 1062303 | 4/1989 |
| JP | 1092403 | 4/1989 |
| JP | 2088626 | 7/1990 |
| JP | 7227403 | 8/1995 |
| JP | 8252281 | 10/1996 |
| JP | 2006280664 | 10/2006 |
| JP | 2007209457 | 8/2007 |
| JP | 2008079867 | 4/2008 |
| WO | 9835642 | 8/1998 |
| WO | 0035397 | 6/2000 |

* cited by examiner

ABSORBENT ARTICLE HAVING A FASTENING SYSTEM WITH LOW STIFFNESS

BACKGROUND

The present disclosure relates generally to absorbent articles intended for personal wear, and more particularly to disposable absorbent articles having a fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

For articles where the attachment is refastenable, such as diapers and some training pants, pop-opens (separation of the fasteners) can sometimes occur as a result of stresses placed on the attachment by movement of the wearer. For example, and particularly for absorbent articles employing only one fastening system, as an infant or other wearer of the absorbent article moves about (e.g., crawls, walks, runs, bends, etc.) the shear stress placed on the fastening system due to the infant's movement may cause fastening tabs or the like to loosen or even come unfastened completely, resulting in an absorbent article which tends to leak, sag, or fall off of a wearer.

Accordingly, some known absorbent articles comprise more than one fastening system and/or fasteners to reduce the likelihood of the article leaking, sagging, falling off the user, etc. For example, FIG. 1 illustrates a known diaper, indicated generally at 10, comprising two fastening systems: a primary fastening system and a secondary fastening system. FIG. 1 depicts the diaper 10 in an unfolded and laid flat condition to show an outer cover 32 of the diaper which faces away from a wearer when the diaper is worn. The diaper 10 has a longitudinal direction 12 and a lateral direction 14.

In the longitudinal direction 12, the diaper 10 defines a front portion 16, a back portion 18, and a crotch portion 20 extending between and connecting the front portion and the back portion. The diaper 10 also includes a bodyside liner 30 (facing away from the view depicted in FIG. 1), and an absorbent core 34 located between the bodyside liner and the outer cover 32. The diaper 10 has opposite longitudinal side edges 28 that extend between a back waist edge 38 and a front waist edge 40. The diaper 10 also includes a pair of longitudinally-extending leg cuffs 36. The leg cuffs 36 may be adapted to fit about the legs of a wearer in use and serve as a mechanical barrier to the lateral flow of body exudates.

The back portion 18 of the diaper 10 includes a pair of back ears, indicated generally at 22. Each ear 22 includes a primary first fastening component 24 as part of the primary fastening system used to secure the diaper 10 around the waist of a wearer. The primary fastening system also comprises a primary second fastening component 76 for selectively receiving and fastening to the primary first fastening components 24. For example, the diaper 10 can be selectively moved from an unfastened configuration (as seen in FIG. 1) to a fastened or wear configuration by attaching the back waist region 18 (and more specifically the back ears 22) to the front waist region 16 to define a three-dimensional wear configuration of the diaper having a waist opening and a pair of leg openings. More particularly, the diaper 10 can be selectively moved from the unfastened configuration to the wear configuration by fastening the primary first fastening components 24 to the primary second fastening components 76 as is well known in the art.

The diaper 10 also includes a secondary fastening system comprising secondary first fastening components 26 and secondary second fastening components 78. For example, the illustrated diaper 10 comprises a pair of secondary first fastening components 26 as part of the front portion 16 of the diaper, with a secondary second fastening component 78 provided on each back ear 22. In such configurations, when the diaper 10 is moved to the wear configuration, the secondary first fastening components 26 engages the back portion 18 of the diaper (and more particularly, the secondary second fastening components 78 provided on the back ears 22) such that both the primary fastening system and the secondary fastening system secure the diaper around the waist of a wearer.

However, providing the secondary first fastening components 26 on the diaper 10 may pose drawbacks when the diaper is packaged or ultimately worn. For example, with respect to packaging, the diaper 10 may be folded when provided to an end user in a package as depicted in FIG. 2. Specifically, during manufacturing, packaging, or the like, the diaper 10 may be first tri-folded by folding the diaper along or near two longitudinal fold lines 42, such that the portions of the diaper provided outwardly of the fold lines (i.e., the portions closest to the longitudinal side edges 28) of the diaper are folded underneath the portion of the diaper located between the two longitudinal fold lines. When folded underneath, the portions disposed outwardly of the fold lines 42 may overlap one another underneath a portion of the diaper 10 containing the absorbent core 34. The diaper 10 may then be bi-folded along or near lateral fold line 44 such that the back waist edge 38 is generally aligned with the front waist edge 40 in the folded configuration.

When the diaper 10 is folded in the conventional manner described above, the secondary first fastening components 26 (which are disposed at or inward of the fold line 42) may be partially or fully disposed on an outside of the folded diaper (as illustrated in FIG. 2). More particularly, and as best seen in FIG. 1, the longitudinal fold lines 42 may be provided outward (i.e., closer to the longitudinal side edges 28) than the edges of the absorbent core 34. However, because the secondary first fastening components 26 are provided near or even abutting the absorbent core 34, the diaper 10 will be folded such that the secondary first fastening components 26 are disposed on or (as illustrated in FIG. 1) even inboard of the fold lines 42. Thus, when the folded diaper 10 is ultimately provided in a stack within a package provided to the end user (as depicted in FIG. 3), the secondary first fastening components 26 will be disposed on the outside of a diaper and may engage an adjoining diaper. More specifically, the secondary first fastening components 26 of a first diaper 10 in a stack may engage the outer cover 32 of an adjoining diaper. Thus, when removing a diaper 10 from the stack of diapers for use, a user may have to forcibly separate the diaper from an adjoining (and attached) diaper. This may result in delaminating, tearing, etc., one or both of the adjoining diapers 10.

Further, because in such a configuration the secondary first fastening components 26 are disposed on the outside of the diaper 10, the folded diaper may engage other diapers or other objects during a packaging process. For example, the diaper 10 may be folded as described and subsequently packaged via, e.g., an automated process, a machine line, a conveyor belt, an assembly line, or the like. When the secondary first fastening components 26 are provided on the outside of the folded diaper 10 as is depicted in FIGS. 2 and 3, during this packaging process (e.g., during movement down a conveyor belt, stacking the diapers in consumer packaging, etc.) the diaper may be prone to catching on other objects and/or other diapers via the exposed secondary first fastening components. This may cause damage to the diapers 10 ultimately packaged and/or cause delays in the manufacturing or packaging process.

Some known diapers avoid such problems by disposing a pair of fastening components (similar to the depicted secondary first fastening components 26) at or near a corresponding side edge 28 of the diaper 10 such that it will ultimately be disposed on an inside of the diaper when folded as described above. However, when such fastening components are disposed at or near the corresponding longitudinal side edge 28, the secondary first fastening component 26 may be prone to engaging a portion the bodyside liner 30 or a containment flap (not shown) of the diaper 10 when in the folded state. This may lead to, e.g., delamination or tearing of the bodyside liner 30 or the containment flap when the diaper 10 is unfolded for use.

Further, in such configurations, one of the secondary first fastening components 26 may engage the bodyside liner 30 and/or a flap, with the other secondary first fastening component engaging the outer cover 32. Thus, when a user unfolds the diaper 10, the user must complete two steps. That is, the user must first separate a first of the secondary first fastening components 26 from the outer cover 32 of the diaper 10 (to unfold the diaper along the lateral fold line 44), and then would need to separate a second of the secondary first fastening components from the bodyside liner 30 and/or flaps (to unfold the diaper along the pair of longitudinal fold lines 42). Thus, in such configurations, the diaper 10 may be difficult to prepare when placing the diaper on a wearer (e.g., an infant).

For example, and returning to FIG. 1, if each secondary first fastening component 26 were disposed at or near a corresponding side edge 28 of the diaper 10 rather than near the absorbent core 34, when the diaper is tri-folded as discussed, each secondary first fastening component would be disposed very near a center line of the diaper at a location where the front portion 16 of the diaper overlaps itself. In such embodiments, one of the secondary first fasteners 26 may engage the bodyside liner 30 (and/or a containment flap, not shown) of the diaper at this overlapping region. In such a configuration, when a user pulls the folded diaper 10 apart for use (i.e., when the user disengages the secondary first fastening components 26 from the bodyside liner 30) the bodyside liner may become delaminated or tear. This may result in the secondary first fastening components 26 retaining residual pieces of the torn bodyside liner 30 (leading to a less effective secondary fastening system), and/or the torn bodyside liner causing discomfort to the wearer, leaking, and/or being aesthetically unpleasing to a user of the diaper 10.

Further, when the secondary first fastening components are disposed at the overlapping region, a first of the secondary first fastening components will be disposed below and overlapped by the front portion 16 of the diaper 10, with a second of the secondary first fastening components disposed on the part of the front portion of the diaper which overlaps the first of the secondary first fastening components and exposed to the outer cover 32. Thus, when folded along the lateral fold line 44, the first of the secondary first fastening components 26 will engage the bodyside liner 30 and/or the flap, while the second of the secondary first fastening components will engage the outer cover 32. Thus, during use, a user must first disengage the second of the secondary first fastening components 26 from the outer cover 32 to unfold the diaper 10 along the lateral fold line 44, and then must disengage the first of the secondary first fastening components from the bodyside liner 30 and/or the flap to unfold the diaper along the longitudinal fold lines 42. Thus, this configuration adds an unfolding step for the user as compared to diapers 10 in which both of the secondary first fastening components 26 engage, e.g., the outer cover 32.

Other known diapers thus attempt to diminish the problems discussed above by disposing the secondary first fastening components 26 outboard of fold lines 42 depicted in FIG. 1 but inboard of the longitudinal side edges 28. For example, Kimberly-Clark de Mexico, S.A.B. de C.V. currently manufactures and makes commercially available a diaper 10 which comprises a pair of secondary first fastening components 26 on the front portion 16 of the diaper 10. See, e.g., Huggies® ultracomfort diaper with the no Velcro® fastening system ("the KC-Mexico diaper"). The pair of secondary first fastening components 26 of the KC-Mexico diaper 10 are positioned very near (and in some embodiments even abut) the longitudinal side edges of an absorbent core 34 of the KC-Mexico diaper. When packaging the KC-Mexico diaper 10, the diaper is folded along the longitudinal edges of the absorbent core 34 such that a portion of the secondary first fastening components 26 are facing an inside of the folded diaper.

However, because the secondary first fastening components 26 are disposed very near (and in some embodiments even abut) the longitudinal sides of the absorbent core 34, when the diaper 10 is folded the entirety of the secondary first fastening components may not be disposed on an inside of the folded diaper, or, alternatively, may be disposed inside the folded diaper but very near or adjacent to a longitudinally extending folded side of the folded diaper. More particularly, the inboard longitudinal edges of the secondary first fastening components 26 of the KC-Mexico diaper 10 (i.e., the longitudinal edges of the secondary first fastening components abutting the absorbent core 34) may be disposed very near, at, or even inside of the fold lines 42 and thus may be prone to being exposed outside of the folded diaper along the folded edges. Thus, the KC-Mexico diaper 10 suffers at least some of the deficiencies described above, including being prone to engaging other diapers, objects, packaging, etc., during manufacturing and packaging the diaper.

Still further, a stiffness or similar properties of the secondary first fastening components 26 may lead to discomfort or decreased mobility for a wearer of the diaper 10. For example, when wearing the diaper 10, an infant may crawl, walk, run, bend, etc., in such a manner that the front portion 16 of the diaper moves, bends, or otherwise deforms. Thus, if the secondary fastening system (and more particularly the secondary first fastening components 26 disposed on the front portion 16 of the diaper 10) is too stiff, the user may have decreased mobility as the front portion of the diaper may not be as readily deformed as if the secondary fastening system was omitted from the diaper. Further, a relatively stiff secondary fastening system may be uncomfortable to a wearer with the relatively unpliable secondary first fastening components 26 providing irritation when the wearer moves.

There is a need, therefore, for an improved fastening system provided on an absorbent article which provides for increased protection against leakage and secure attachment of the absorbent article without the associated discomfort and/or packaging and manufacturing drawbacks discussed above.

SUMMARY

In one aspect, an absorbent article is provided. The absorbent article general comprises an inner surface, an outer surface, a first waist portion, a second waist portion, and a crotch portion extending longitudinally between and connecting the first waist portion and the second waist portion. The absorbent article further comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. The absorbent article further comprises a pair of ears extending transversely outward from the opposite sides of the chassis at the second waist portion thereof, and a fastening system. The fastening system generally comprises a primary fastening system and a secondary fastening system. The primary fastening system includes a primary first fastening component disposed on each of the pair of ears and a primary second fastening component disposed on the outer surface of the article at the first waist portion. The secondary fastening system includes a secondary second fastening component on each of the pair of ears and a corresponding secondary first fastening component on the outer surface of the article at the first waist portion. Each of the secondary first fastening components has a stiffness in the longitudinal direction of the article of less than 185 milligrams according to a Gurley Stiffness Test.

In another aspect, an absorbent article is provided. The absorbent article generally comprises an inner surface, an outer surface, a first waist portion, a second waist portion, and a crotch portion extending longitudinally between and connecting the first waist portion and the second waist portion. The absorbent article further comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. The absorbent article further includes a pair of ears extending transversely outward from the opposite sides of the chassis at the second waist portion thereof, and a fastening system. The fastening system generally comprises a primary fastening system and a secondary fastening system. The primary fastening system comprises a primary first fastening component disposed on each of the pair of ears and a primary second fastening component disposed on the outer surface of the article at the first waist portion. The secondary fastening system comprises a secondary second fastening component on each of the pair of ears and a corresponding secondary first fastening component on the outer surface of the article at the first waist portion. Each of the secondary first fastening components has a peak load corresponding to an edge stiffness in the longitudinal direction of the article of less than 100 grams-force according to an Edge Stiffness Test.

In yet another aspect, an absorbent article is provided. The absorbent article generally comprises an inner surface, an outer surface, a first waist portion, a second waist portion, and a crotch portion extending longitudinally between and connecting the first waist portion and the second waist portion. The absorbent article further comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. The absorbent article further includes a pair of ears extending transversely outward from the opposite sides of the chassis at the second waist portion thereof, and a fastening system. The fastening system generally comprises a primary fastening system and a secondary fastening system. The primary fastening system includes a primary first fastening component disposed on each of the pair of ears and a primary second fastening component disposed on the outer surface of the article at the first waist portion. The secondary fastening system comprises a secondary second fastening component on each of the pair of ears and a corresponding secondary first fastening component on the outer surface of the article at the first waist portion. Each of the secondary first fastening component has a peak stress corresponding to an edge stiffness in the longitudinal direction of the article of less than 8.5 grams-force per square millimeter according to an Edge Stiffness Test.

In still another aspect, an absorbent article is provided. The absorbent article generally comprises an inner surface, an outer surface, a first waist portion, a second waist portion, and a crotch portion extending longitudinally between and connecting the first waist portion and the second waist portion. The absorbent article further comprises a chassis having longitudinally opposite ends, transversely opposite sides, a bodyside liner at least in part defining the inner surface of the article, an outer cover at least in part defining the outer surface of the article, and an absorbent core disposed between the liner and the outer cover. The absorbent article further includes a pair of ears secured to and extending transversely outward from the opposite sides of the chassis at the second waist portion thereof, and a fastening system. The fastening system generally comprises a primary fastening system and a secondary fastening system. The primary fastening system includes a primary first fastening component disposed on each of the pair of ears and a primary second fastening component disposed on the outer surface of the article at the first waist portion. The secondary fastening system comprising a secondary second fastening component on each of the pair of ears and a corresponding secondary first fastening component on the outer surface of the article at the first waist portion. Each of the secondary first fastening components has a Gurley stiffness in the longitudinal direction of the article of less than 185 milligrams according to a Gurley Stiffness Test and a peak load corresponding to an edge stiffness in the longitudinal direction of the article of less than 100 grams-force according to an Edge Stiffness Test.

BRIEF DESCRIPTION OF THE DRAWINGS

Corresponding reference characters indicate corresponding parts throughout the several views of the drawings.

DETAILED DESCRIPTION OF THE DRAWINGS

According to some aspects of the disclosure, an absorbent article is provided which overcomes at least some of the deficiencies of the conventional diapers described above. More particularly, according to some aspects of the disclosure, the absorbent article includes a secondary fastening system in order to securely attach the absorbent article around the waist of a wearer, but which comprises improved pliability over known fastening systems such that the absorbent article remains securely fastened even as the wearer crawls, walks, runs, bends, etc. The secondary fastening system may be constructed of suitable materials and disposed in a suitable position relative to other components of the absorbent article such that the absorbent article may be readily packaged or used without the drawbacks of the known diapers discussed above.

Figure 4:
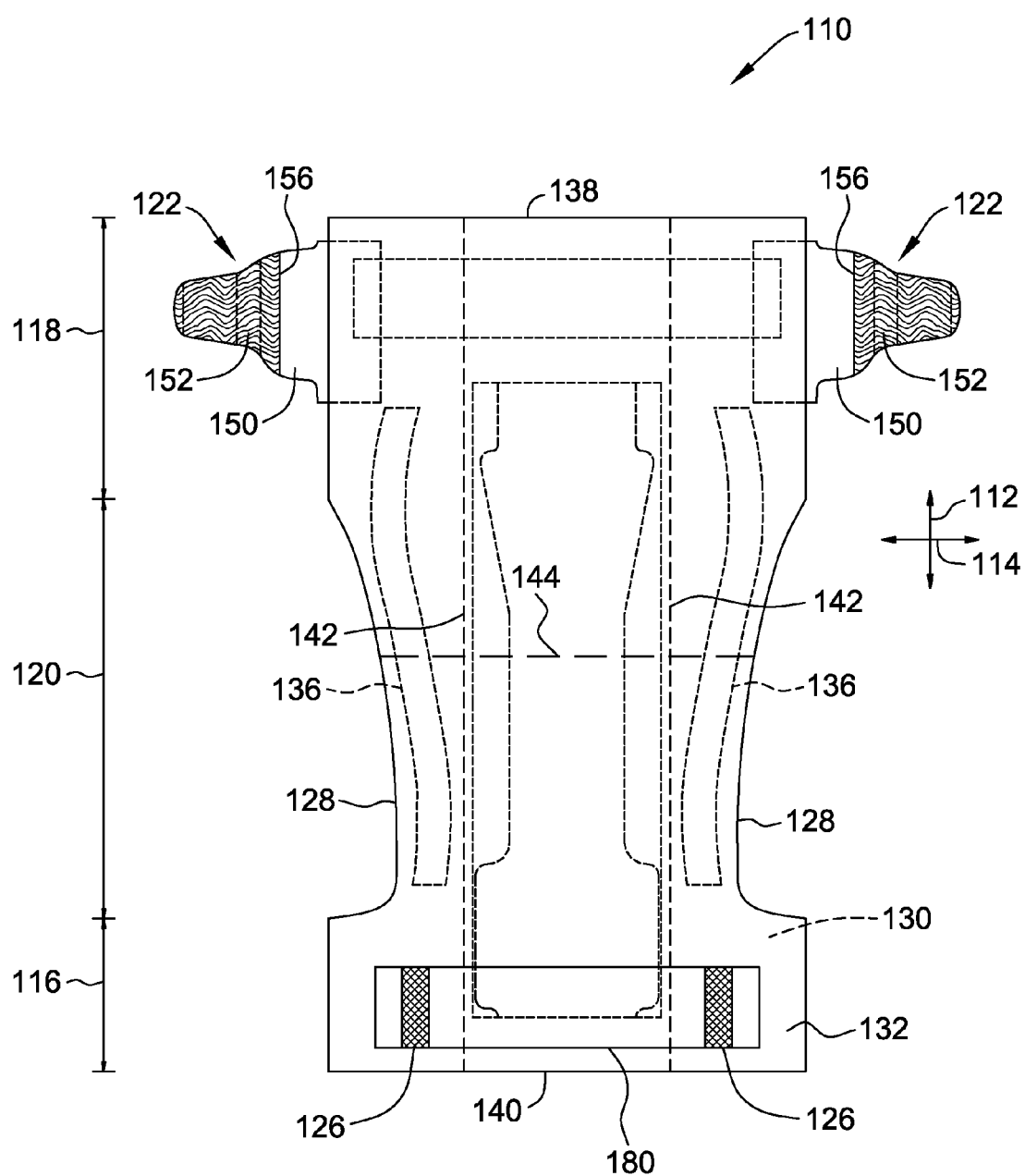
FIG. 4 is a top plan view of a diaper according to one embodiment of the present disclosure in an unfolded and laid flat condition to show an outer surface of the diaper which faces away from the wearer when the diaper is worn.
Figure 5:
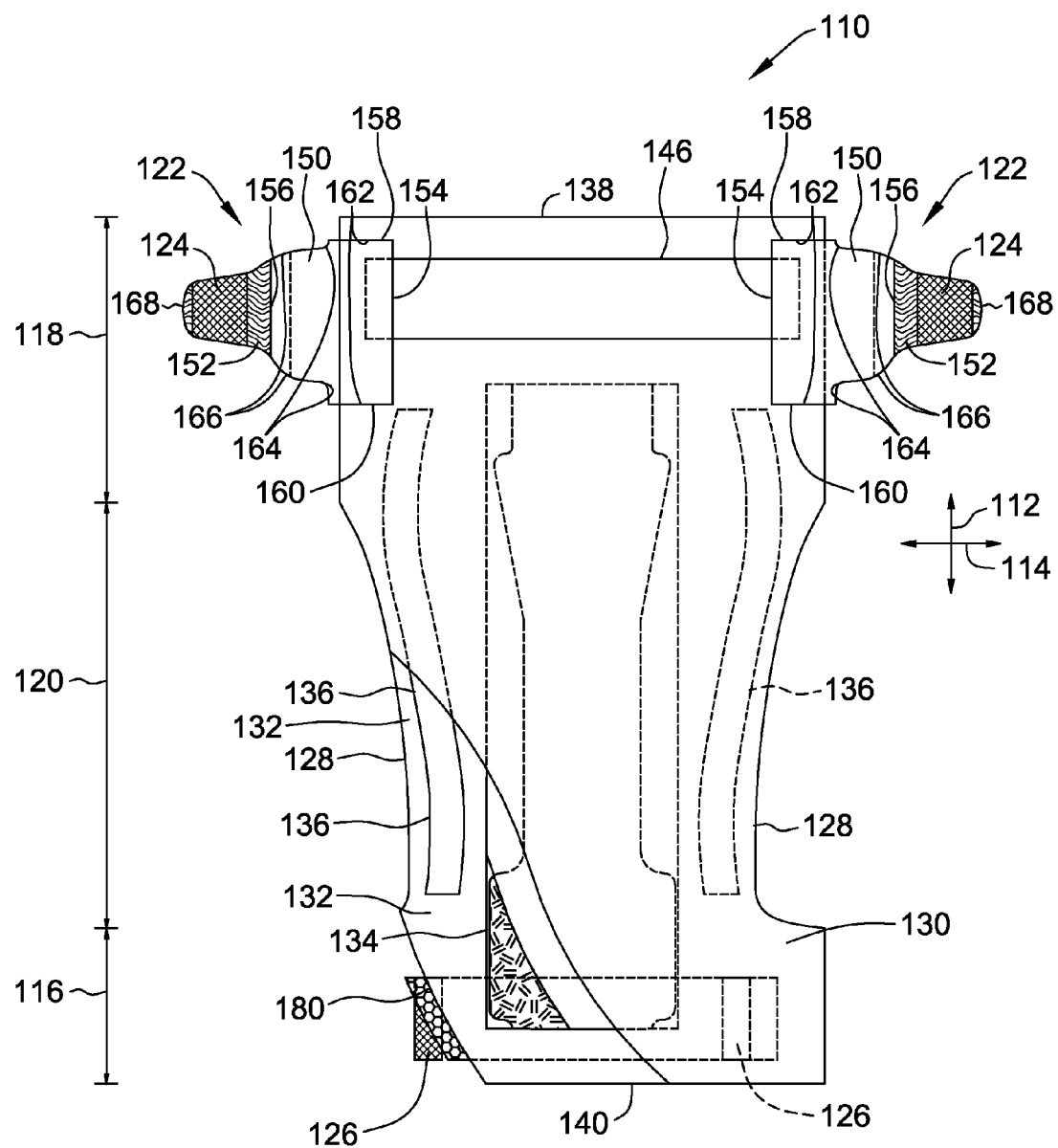
FIG. 5 is a bottom plan view of the diaper of FIG. 4 in an unfolded and laid flat condition to show an inner surface of the diaper which faces towards the wearer when the diaper is worn.

These features will become more apparent with reference to the accompanying drawings. FIGS. 4 and 5 illustrate one suitable embodiment of a diaper (broadly, "an absorbent article"), indicated generally at 110, in an unfolded and laid flat condition to show an outer surface of the diaper which faces away from the wearer when the diaper is worn (FIG. 4) and an inner surface of the diaper which faces the wearer when the diaper is worn (FIG. 5). Portions of the diaper 110 illustrated in FIG. 5 are cut away to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like.

In one suitable embodiment, the diaper 110 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 110 can be reusable. That is, the diaper 110 can be intended for multiple uses without departing from some aspects of this disclosure.

Figure 16:
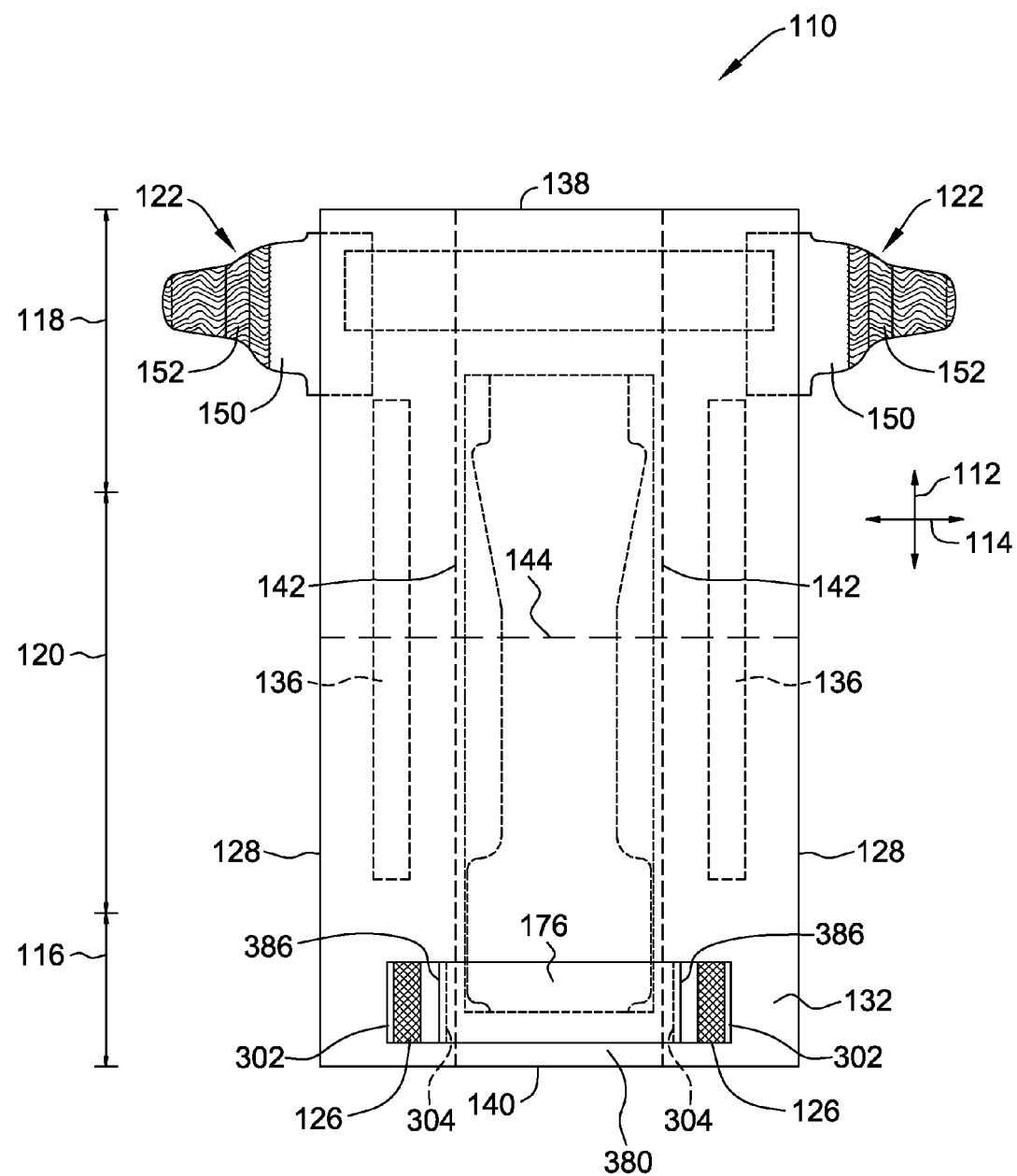
FIG. 16 is a top plan view of a diaper according to still another embodiment in an unfolded and laid flat condition to show an outer surface of the diaper which faces away from the wearer when the diaper is worn.

In the longitudinal direction 112, the diaper 110 defines a front portion 116, a back portion 118, and a crotch portion 120 extending between and connecting the front portion and the back portion. The diaper 110 includes a bodyside liner 130, an outer cover 132, and an absorbent core 134 located between the bodyside liner and the outer cover. The bodyside liner 130, outer cover 132 and absorbent core 134 collectively define an absorbent assembly. The absorbent assembly can be any suitable shape including, for example, generally I-shaped as illustrated in FIGS. 4 and 5 or generally rectangular as illustrated in FIG. 16. As used herein, reference to the front portion 116 refers to that part of the diaper 110 which is generally located on the front of a wearer when in use. Reference to the back portion 118 refers to the portion of the diaper 110 generally located at the back of the wearer when in use, and reference to the crotch portion 120 refers to that portion which is generally located between the legs of the wearer when in use.

In the illustrated embodiment, the back portion 118 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 may be cut in any suitable shape as are known in the art (e.g., arcuate). As seen in FIGS. 4 and 5, the diaper 110 has opposite longitudinal side edges 128 that extend between the back waist edge 138 and the front waist edge 140. In the illustrated embodiment, each of the side edges 128 include an arcuate portion for defining a portion of a leg opening during wear of the diaper 110.

The bodyside liner 130 of the diaper 110, as illustrated in FIG. 5, defines a body facing surface that is intended to be worn adjacent and in directed contact with the body of the wearer. The bodyside liner 130 is suitably compliant, soft feeling and nonirritating to the wearer's skin. The bodyside liner 130 is less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134.

The outer cover 132 of the diaper 110, which is illustrated in FIG. 4, defines a garment facing surface which is intended to be worn adjacent the clothing of the wearer. In one suitable embodiment, the outer cover 132 is a polyethylene film. In another suitable embodiment, the outer cover 132 comprises a woven or non-woven fibrous web layer which has been totally or partially constructed or treated to impart a desired level of liquid impermeability to selected regions of the outer cover that are adjacent or proximate the absorbent core 134. For example, a clothlike outer cover may be composed of polypropylene spunbond fabric which is laminated and thermally bonded to a stretch-thinned polypropylene film. The outer cover 132 may include a micro-porous, "breathable" material which permits vapors to escape from diaper 110 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 may have any of a number of shapes and sizes. For example, the composite absorbent core 134 may be rectangular, I-shaped, or T-shaped. The size and absorbent capacity of the absorbent core 134 should be compatible with the size of the intended wearer and the fluid loading imparted by the intended use of the diaper.

In one suitable embodiment, the diaper 110 may include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion may be a layer of a spunbonded or meltblown web of polyolefin fibers. The surge portion may also be a bonded carded web of natural and synthetic fibers. The surge portion may be a substantially hydrophobic material and, optionally, can be treated with a surfactant or otherwise to impart a desired level of wettability and hydrophilicity.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable embodiment, the leg cuffs 136 can be formed by portions of the outer cover 132, and/or bodyside liner 130, which extend beyond the longitudinal sides of the absorbent core 134. In another suitable embodiment, the leg cuffs 136 can be formed from separate materials (e.g., stands of leg elastics) joined to the outer cover 132 and/or the bodyside liner 130.

The diaper 110 may further include a front waist elastic (not shown) and/or a back waist elastic 146. In the illustrated embodiment, for example, the diaper 110 has a back waist elastic 146 but not a front waist elastic. The back waist elastic 146 is arranged to draw and hold the diaper 110 against the wearer, particularly against the waist of the wearer, as will be more fully discussed.

Materials suitable for use in forming leg cuffs 136 and/or waist elastics 146 are known to those skilled in the art. Examples of such materials are strands or ribbons of a polymeric, elastomeric material which are adhered to the diaper 110 in a stretched position, or which are attached to the diaper while the diaper is pleated, such that elastic constrictive forces are imparted to the diaper. The leg cuffs 136 and/or waist elastics 146 may have any configuration which provides the desired performance. The leg cuffs 136 may be generally straight or optionally curved (as illustrated in FIGS. 4 and 5) to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 may be attached to the diaper 110 in any way known to those skilled in the art. For example, the leg cuffs 136 and/or waist elastics 146 may be joined to the diaper 110 by ultrasonic bonding, thermal bonding, adhesive bonding, and the like, and combinations thereof.

The diaper 110 may also include a pair of containment flaps (not shown) that extend longitudinally along the diaper and are adapted to provide a barrier to the lateral flow of body exudates. The containment flaps can be connected to the bodyside liner 130 or other components as is well known in the art. Suitable configurations of the containment flaps 148 are described, for example, in U.S. Pat. No. 5,599,338 issued Feb. 4, 1997, to K. Enloe, the entirety of which is incorporated herein by reference.

As seen in FIGS. 4 and 5, the back portion 118 of the diaper includes a pair of back ears, indicated generally at 122. In one suitable embodiment, the back ears 122 can be formed from extensions of the bodyside liner 130, the outer cover 132, or combinations of both the bodyside liner and the outer cover. In another suitable embodiment, and as illustrated in FIGS. 4 and 5, the back ears 122 can be formed as separate components and attached to the bodyside liner 130, the outer cover 132, or both the bodyside liner and the outer cover as is known in the art. In the illustrated embodiment, the back ears 122 are attached to the body-facing surface of the bodyside liner 130 such that the attached portion of the ears 122 are disposed between the wearer's body and bodyside liner when the diaper 110 is worn.

In one suitable embodiment, each of the back ears 122 includes an elastomeric portion 150, a non-elastomeric portion 152, and a primary first fastening component 124 mounted to the non-elastomeric portion (FIG. 5). Each of the elastomeric portions 150 has a proximal edge 154, an opposed distal edge 156, an upper edge 158, and a lower edge

160. As seen in FIG. 5, the proximal edge 154 of each of the elastomeric portions 150 is spaced inward from the respective side edge 128 of the diaper 110 such that a portion of the elastomeric portion overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner. In another suitable embodiment, the elastic component 150 may be eliminated and the entire back ear 122 may be constructed from the non-elastic component 152.

In the embodiment illustrated in FIGS. 4 and 5, the proximal edge 154 and the distal edge 156 of each of the elastomeric portions 150 are generally parallel with respect to each other, and both are straight (i.e., linear). In one suitable embodiment, the proximal edge 154 has a length from about 2 inches (5.1 centimeters) to about 7 inches (17.8 centimeters), preferably from about 3 inches (7.6 centimeters) to about 6 inches (15.2 centimeters), and more preferably from about 3.5 inches (8.9 centimeters) to about 5.5 inches (14.0 centimeters). The distal edge 156 has a length from about 0.25 inch (0.635 centimeter) to about 6 inches (15.24 centimeters), and preferably from about 1 inch (2.54 centimeters) to about 3 inches (7.6 centimeters). Further, the ratio of the length of the distal edge 156 to the proximal edge 154 is suitably from about 1:28 to about 3:4, and, and preferably from about 1:10 to about 2:3, and more preferably from about 1:4 to about 1:2.

Both the upper and lower edges 158, 160 have first segments 162 that are generally parallel to each other and generally perpendicular to the respective proximal edges 154. Each of the first segments 162 generally correspond to the part of each of the elastomeric portions 150 that overlap the bodyside liner 130. In the illustrated embodiment, the first segments 162 of the upper edges 158 of the elastomeric portion 150 are spaced from the back waist edge 138. It is understood, however, that the first segments 162 can be aligned with the back waist edge 138 of the diaper 110.

Second segments 164 of each of the upper and lower edges 158, 160 are generally coaxial and extend towards each other generally perpendicular to the first segments 162. In the illustrated embodiment, the second segment 164 of the lower edge 160 has a length greater than the length of the second segment of the upper edge 158. It is understood, however, that the second segments 164 of the upper and lower edges 158, 160 can have any suitable length.

Each of the illustrated elastomeric portions 150 includes an arcuate third segment 166 interconnecting the second segments 164 to the respective distal edge 156. In the illustrated embodiment, the third segments 166 are generally mirror images of each other. It is understood, however, that the third segments 166 can have any suitable shape and that the third segments of the upper edges 158 can have a shape that is different that the shape of the third segments of the lower edges 160.

The elastomeric portions 150 of the back ears 122 can be formed from any type of elastomeric material capable of performing as described herein. In one suitable embodiment, the elastomeric material will be stretchable in at least one direction (e.g., in the lateral direction 114 of the diaper 110 as viewed in FIGS. 4 and 5) and alternatively, the elastomeric material will be stretchable in two directions (e.g., in both the longitudinal direction 112 and the lateral direction of the diaper as viewed in FIGS. 4 and 5). Suitably when the elastomeric material is stretchable in a single direction, the stretch direction of the elastomeric material will be oriented so as to provide elastomeric forces which tend to pull the front and rear portions of the article towards one another such that the article is maintained about the waist of a wearer.

In one suitable embodiment, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions. As illustrated in FIGS. 4 and 5, the non-elastomeric portions 152 of the back ears 122 extend in part transversely outward of the respective elastomeric portion 150 and the primary first fastening component 124 of each of the non-elastomeric portions are configured for engaging a loop component disposed in the front waist region 116 of the diaper 110 in the wear configuration, as will be discussed more fully.

As seen best in FIG. 5, each of the illustrated non-elastomeric portions 152 further comprise a grip region 168 transversely outward of the primary first fastening component 124 for use in manually gripping and manipulating the non-elastomeric portion and more broadly the respective back ear 122 relative to the diaper 110. The grip region 168 is non-attachable to the diaper 110. The term "non-attachable" as used in this instance means that the grip region 168 is not releasably or otherwise removably attachable to the diaper 110. In one embodiment, the grip region 168 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

Figure 6:
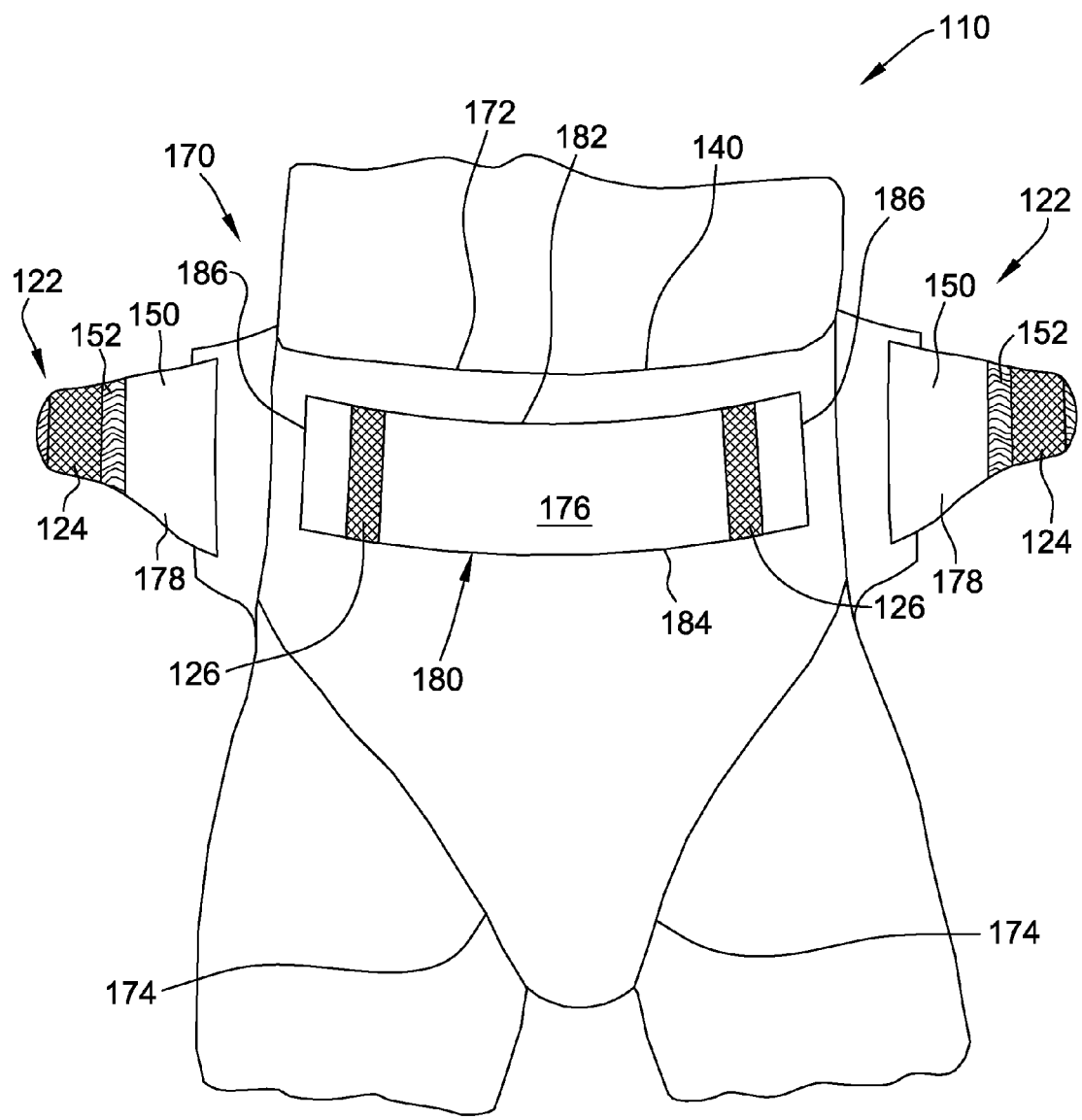
FIG. 6 is a front view of the diaper of FIG. 4 in a wear configuration with the fastening system not fastened.
Figure 7:
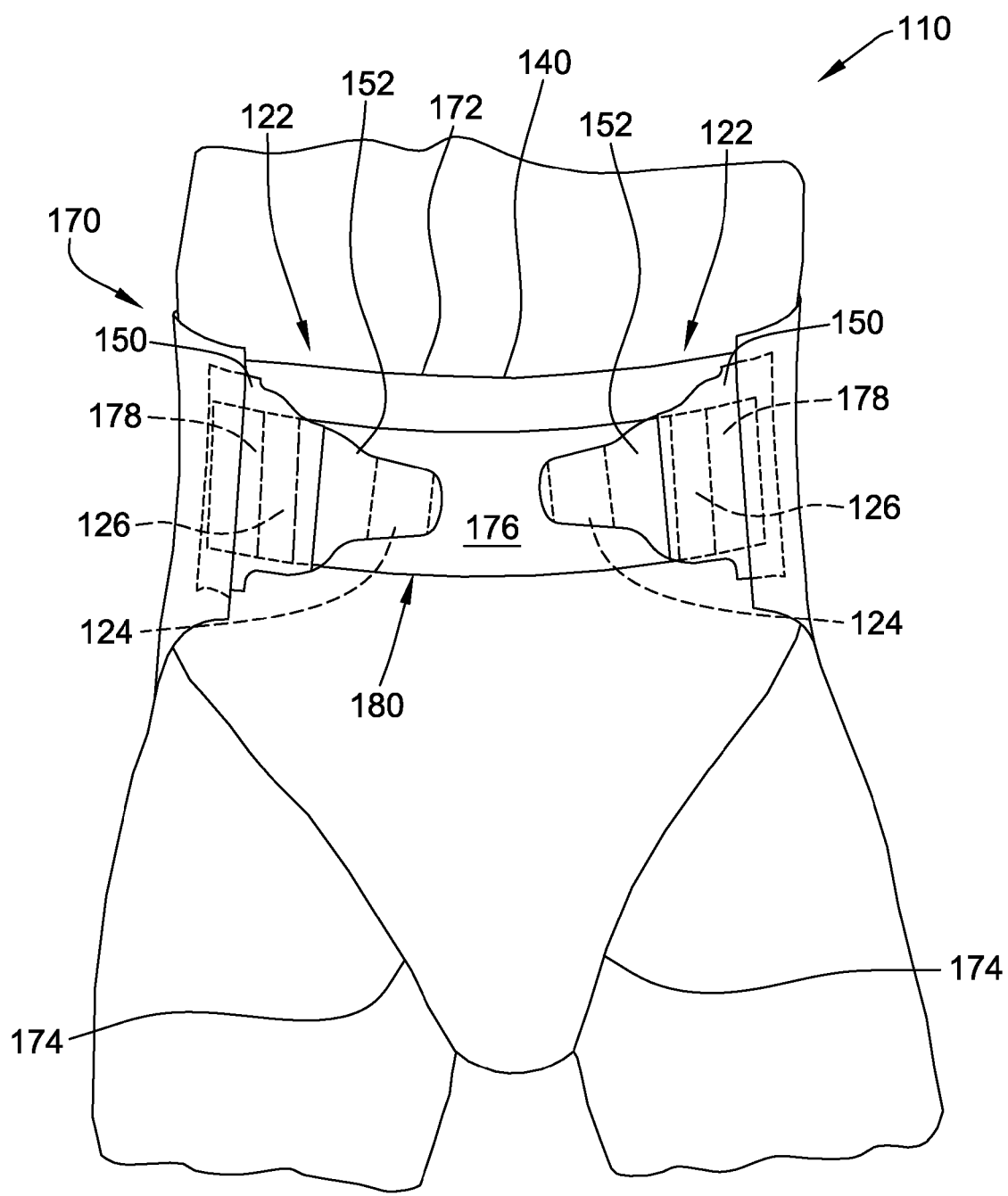
FIG. 7 is a front view of the diaper of FIG. 4 in a wear configuration with the fastening system fastened.

The diaper 110 can be selectively moved from the unfastened configuration, as illustrated in FIGS. 4 and 5, to a fastened or wear configuration as illustrated in FIGS. 6 and 7, by attaching the back waist region 118 (and more specifically the back ears 122) to the front waist region 116 using an article fastening system 170 to define a three-dimensional wear configuration of the diaper having a waist opening 172 and a pair of leg openings 174. Although the diaper 110 illustrated in FIGS. 6 and 7 shows the back waist region 118 (and more specifically the back ears 122) overlapping the front waist region 116 upon connection thereto, which is convenient, the diaper can also be configured so that the front waist region overlaps the back waist region when connected.

According to some embodiments, the article fastening system 170 comprises a primary fastening system and a secondary fastening system. The primary fastening system comprises the primary first fastening components 124 disposed on the non-elastomeric portions 152 of the back ears 122 and at least one corresponding primary second fastening component 176 which is adapted for refastenable engagement to the primary first fastening components. In one suitable embodiment, an outer surface of each of the primary fastening components 124, 176 comprises a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 may comprise any refastenable fasteners suitable for absorbent articles, such as adhesive fasteners, cohesive fasteners, mechanical fasteners, or the like. In one suitable embodiment, the primary fastening components 124, 176 comprise mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated embodiment, the primary first fastening components 124 comprise hook fasteners and the primary second fastening components 176 comprise a complementary loop fastener disposed on the outer surface of the outer cover 132. Alternatively, the primary first fastening components 124 may comprise loop fasteners and the primary second fastening components 176 may comprise complementary hook fasteners.

The shape, density, and polymer composition of the hooks and loops may be selected to obtain the desired level of engagement between the primary fastening components 124, 176. A more aggressive hook material may comprise a material with a greater average hook height and/or a greater percentage of directionally-aligned hooks.

In some embodiments, the outer facing surface of the outer cover 132 of the diaper 110 is suitably constructed to define the primary second fastening component 176, which is a loop fastener. That is, the outer cover 132 itself can be formed of a material that defines the primary second fastening component 176 (e.g., vertical filament laminate (VFL) or other suitable material).

In another suitable embodiment, and as illustrated in FIG. 6, the primary second fastening component 176 can be formed as a separate component and attached to the outer surface of the diaper's outer cover 132. More specifically, a strip, indicated generally at 180, comprising loop fastening material is attached to the front waist region 116 of the diaper. The strip 180 comprises an upper edge 182, a lower edge 184, and a pair of side edges 186 connecting the upper and lower edges 182, 184. The upper edge 182 is spaced from the front waist edge 140 and the side edges 186 are spaced from the respective side edges 128 of the diaper 110.

The secondary fastening system of the article fastening system 170 comprises secondary first fastening components 126 and secondary second fastening components 178. The secondary first fastening components 126 are disposed on the front portion 116 of the diaper 110 and are adapted for refastenable engagement to at least one corresponding secondary second fastening component 178 (e.g., the elastomeric portion 150 of the back ears 122). As best seen FIG. 6, in some embodiments, the strip 180 may comprise the pair of spaced-apart secondary first fastening components 126.

In the illustrated embodiment, the secondary first fastening components 126 comprise hook fasteners and are configured to engage the secondary second fastening components 178 in the wear configuration of the diaper 110. Again, as used herein "hook" fasteners refers broadly to any suitable mechanical fastener adapted to engage loop components including, e.g., hooks, bulbs, mushrooms, arrowheads, balls on stems, stems, structures having stems that engage foam such as open cell foam or the like, etc. In one embodiment, the secondary first fastening components 126 may be constructed of polyethylene or other suitable polymer blends. In one suitable embodiment, the elastomeric portions 150 of the back ears 122 are constructed so at least the inner surfaces of the elastomeric portions define the secondary second fastening components 178 in the form of loop fastening components (i.e., the elastomeric portions and the respective secondary second fastening components are formed integrally). The elastomeric portions 150 in one suitable embodiment can be constructed of NBL material so that the elastomeric portions itself defines a loop fastening component. In another suitable embodiment, the elastomeric portions 150 can be constructed of VFL material so that the elastomeric portions itself defines a loop fastening component. It is understood, however, that the secondary second fastening components 178 may be formed separate from the elastomeric portions 150 and attached thereto, such as by adhesive, thermal bonds, ultrasonic bonds, pressure bonds, or other suitable techniques without departing from the scope of this disclosure.

In other suitable embodiments, the secondary first fastening components 126 may comprise loop fasteners and the secondary second fastening components 178 may comprise loop fasteners. Further, in some embodiments the secondary first fastening components 126 may be a single, integral fastener. For example, in one suitable embodiment the secondary first fastening components 126 may be a single, loop fastener, and the secondary second fastening components 178 may be loop fasteners.

In one suitable embodiment, the strip 180 comprising both the secondary first fastening components 126 and the primary second fastening component 176. In one such embodiment where the primary second fastening component 176 comprises a loop material and the secondary first fastening component 126 comprises a hook material, the strip 180 may be a suitable loop material (forming the primary second fastening component), and then the hook material may be extruded onto the loop material at two or more locations forming the secondary first fastening components.

In another suitable embodiment, the secondary first fastening components 126 can be formed separate from the primary second fastening component 176. In such an embodiment, the primary second fastening component 176 can be formed to define the strip 180 and the secondary first fastening components 126 can be attached in overlaying relationship with portions of the primary second fastening component. In such embodiments, the secondary first fastening components 126 may be attached to the strip 180 and/or the primary second fastening component 176 using any suitable means known to those skilled in the art, including, e.g., adhesive bonds, ultrasonic bonds, thermal bonds, pressure bonds, and the like, and combinations thereof.

In some embodiments, the secondary first fastening components 126 may be attached to the diaper 110 and/or the strip 180 after the strip has been attached to the diaper 110. For example, in one suitable embodiment the strip 180 may be first bonded to the diaper 110 using any suitable means as discussed, and then the secondary first fastening components 126 may be bonded to or extruded on the strip. In other embodiments, the strip 180 comprising both the secondary first fastening components 126 and primary second fastening components 176 can be attached to the diaper 110 as one single unit.

According to some embodiments, the secondary first fastening components 126 and/or the strip 180 may be sufficiently bonded to the diaper 110 such that a shear force exerted on the secondary first fastening components and/or the strip during use of the diaper does not cause the secondary first fastening components and/or the strip to loosen or completely disengage from the diaper. For example, in some embodiments an improved adhesive or the like can be used such that the secondary first fastening components 126 and/or the strip 180 remain securely fastened to, e.g., the outer cover despite the forces exerted on the fastening system 170 during use. In such embodiments, the diaper 110 may be less prone to pop-opens and the edges of the secondary first fastening components 126 and/or the strip 180 may remain flush with the outer cover 132 thus reducing irritation during wear which may otherwise be caused by a loose secondary first fastener and/or a loose strip.

When the diaper 110 is moved to the wear configuration with the primary fastening components 124, 176 engaging one another, the secondary fastening components 126, 178 may also engage one another in order to provide increased stability and leakage protection. For example, because the article fastening system 170 comprises four engagement points, the diaper 110 will be less prone to pop-opens when worn. Further, because the secondary fastening components 126, 178 engage each other closer to a side of a wearer than an engagement point of the primary fastening components 124, 176, the secondary fastening system secures the diaper 110 nearer the wearer's sides and legs thus reducing leakage near the leg openings 174 of the diaper. Still further, and again because the secondary fastening components 126, 178 engage each other near a side of the wearer, the secondary fastening system may provide increased stability, thus reducing the occurrence of, e.g., sagging of the diaper due to movement of the wearer.

In some embodiments, an appearance of the secondary first fastening component 126, the secondary second fastening component 178, and/or the back ears may be configured to provide suitable visual cues to a user for attaching the diaper 110 to a wearer. For example, in some embodiments, a coloring of the secondary first fastening components 126 may be such so as to, e.g., increase the noticeability of the secondary first fastening components on the front portion 116 of the diaper 110. For example, each of the secondary first fastening components 126 may be configured as a different color than its immediate surroundings such that it stands out from its immediate surroundings. Similarly, a graphic, background pattern, etc., may be removed from the area surrounding the secondary first fastening components 126 to increase the noticeability of each component. Still further, an area on the front portion 116 of the diaper 110 where a corresponding secondary first fastening component 126 attaches may be provided with a different graphic or coloring, etc., than its surrounding, and the secondary first fastening components can correspondingly be constructed of a transparent or semi-transparent material such that, when the secondary first fastening component is provided on the front portion by any suitable means discussed herein, the different coloring, graphical properties, etc., are visible through the secondary first fastening component thus increasing the noticeability of the secondary first fastening components on the front portion.

In still further embodiments, the opacity of the pair of back ears 122 and/or the secondary second fastening component 178 may be configured such that each secondary first fastening component 126 is visible through a respective one of the ears 122 when the diaper 110 is in the wear configuration. For example, in some embodiments the back ears 122 and/or the secondary second fastening components 178 may be transparent or semi-transparent. In such embodiments, the secondary first fastening components 126 may be visible through the back ears 122 when the diaper is in the wear configuration so that a user may be provided with a visual indication of the engagement of each secondary first fastening component with the respective secondary second fastening component 178. In some embodiments, these visual cues (i.e., the coloring or graphical properties of the secondary first fastening component 126 and/or the opacity of the secondary second fastening component 178) may assist a user engaging the secondary fastening system and/or in ensuring the secondary fastening system is properly engaged in the wear configuration.

According to some aspects, the secondary first fastening components 126 may be disposed on the front portion 116 of the diaper 110 at a position relative to the absorbent core 134, longitudinal fold lines 142, and/or the longitudinal side edges 128 such that the secondary first fastening components are provided on an inside of the diaper when folded and such that the secondary first fastening components engage the outer cover 132 and/or the back ears 122 of the diaper when the diaper is folded, the benefits of which will be discussed more fully. This may be more readily understood with reference to FIGS. 8A-11.

Figure 8A:
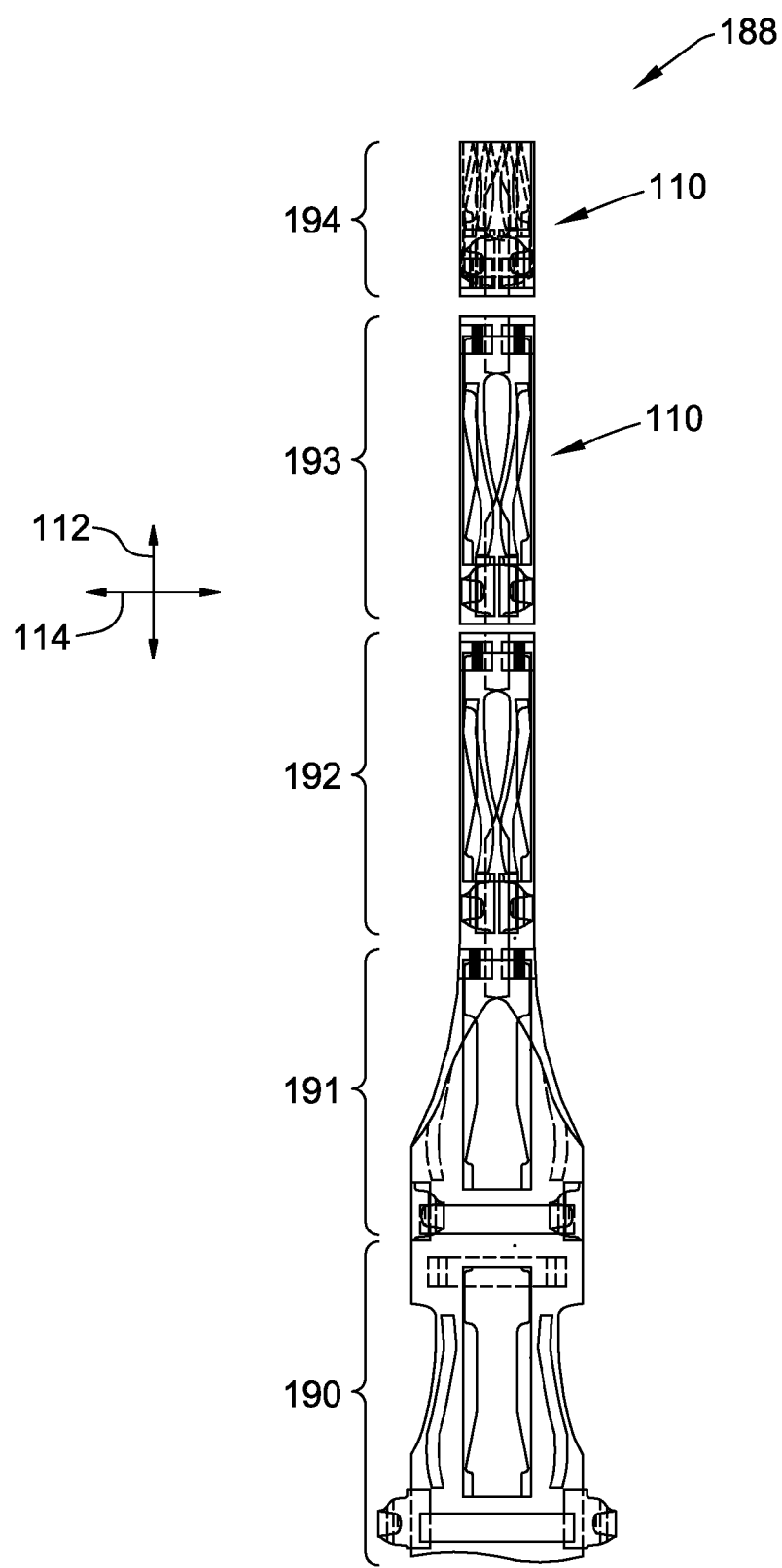
FIG. 8A is a schematic illustrating one suitable folding process of the diaper of FIG. 4.

FIG. 8A illustrates one suitable folding process for the diaper 110. As seen in FIG. 8A, the diaper 110 may be constructed from a continuous length of absorbent articles 188. The length of absorbent articles 188 may be fed in either a machine direction (i.e., longitudinal direction 112) or a cross-machine direction on a machine line or the like and folded as depicted and then separated into individual diapers 110 as is well known in the art. It is understood that the individual diapers 110 can be separated from the continuous length of absorbent articles 188 prior to the diaper being folded.

Figure 10:
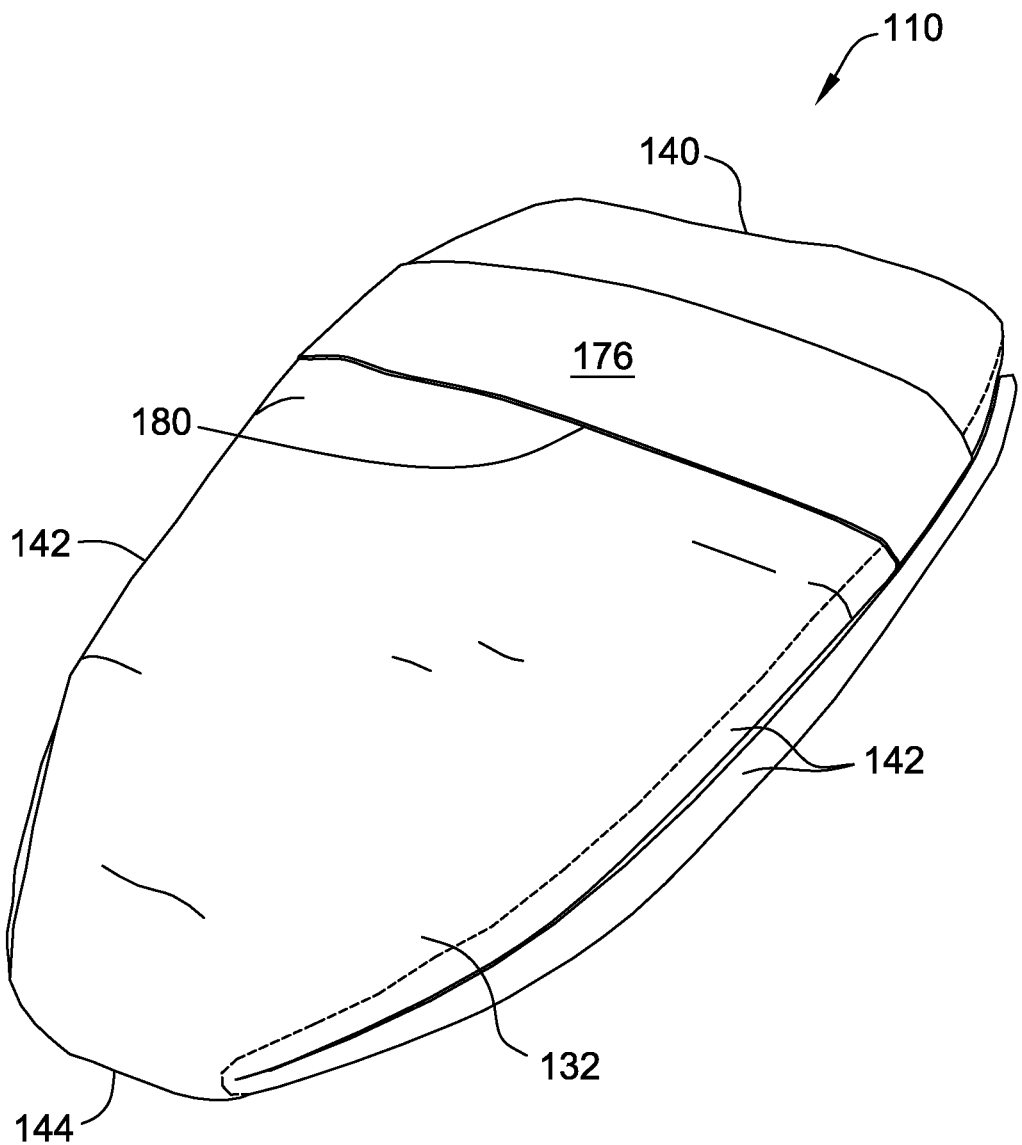
FIG. 10 is a perspective view of the diaper of FIG. 4 in a folded state.

The depicted folding process of FIG. 8A comprises a series of folding steps 190-194 to move the diaper 110 from a substantially flat configuration (as depicted in FIGS. 4 and 5) to a folded configuration (as depicted in FIG. 10). In the first folding step 190, the back ears 122 are folded over on themselves. More particularly, in the first folding step the outermost portions of the back ears 122 (i.e., portions of the back ears comprising the grip regions 168 and at least part of the primary first fastening components 124) are folded toward the bodyside liner 130. In some embodiments, the portion of each back ear 122 folded over in step 190 may engage another portion of corresponding the back ear which is not folded over. For example, in some embodiments at least part of the primary first fastening component 124 of each back ear 122 when folded over may engage a part of the elastomeric region 150, the non-elastomeric region 152, and/or the secondary second fastening component 178 provided at each back ear. In one suitable embodiment, the entire primary first fastening component 124 of each back ear 122 is folded over and engaged with the secondary second fastening component 178 of the same back ear.

In the second folding step 191, the folded over back ears 122 are then again folded onto the absorbent components of the diaper 110 (i.e., the folded over ears are folded over the main body generally at a location of the longitudinal side edges 128). At such a step, portions of the folded over back ears 122 may further overlap portions of the bodyside liner 130. In one suitable embodiment, no portions of the back ears 122 will engage the bodyside liner 130 following the second folding step 191 since the primary first fastening components 124 are engaged with the respective secondary second fastening components 178.

Also at the second folding step 191, the front portion 116 of the diaper 110 is folded such that the longitudinal edges of the front portion overlap one another near a center line 198 of the diaper. More particularly, a first of the two longitudinal edges 128 of the diaper 110 is folded toward the bodyside liner 130 of the diaper such that the first longitudinal edge extends past the center line 198 of the diaper, with the second of the two longitudinal edges then folded over in a similar manner to form an overlap region 196 near the center line of the diaper. At the overlap region 196, a rightmost and leftmost portion of the front portion 116 of the diaper 110 overlap one another with a portion of the bodyside liner 130 abutting a portion of the outer cover 132 (as viewed in FIG. 9A). This will be discussed more fully with reference to FIG. 9A.

In the third folding step 192, the back portion 118 of the diaper is folded over in a similar manner to the front portion 116 as folded in step 191. More particularly, a first of the two longitudinal edges 128 at the back portion 118 of the diaper 110 is first folded toward the bodyside liner 130 of the diaper 110 such that the first longitudinal edge extends past the center line 198 of the diaper, with the second of the two longitudinal edges then folded over in a similar manner to form the overlap region 196 near the center line 198 of the diaper where a rightmost and leftmost portion of the back portion 118 of the diaper overlap one another (as viewed in FIG. 9A).

As seen in FIG. 8A, at the fourth folding step 193, the diaper 110 is removed from the length of absorbent articles 188 by, e.g., cutting the diaper along the back waist edge 138 of the leading diaper and the front waist edge 140 of the trailing diaper. The diaper 110 may be cut from the length of absorbent articles 188 at step 193 by any suitable means well known in the art.

Figure 11:
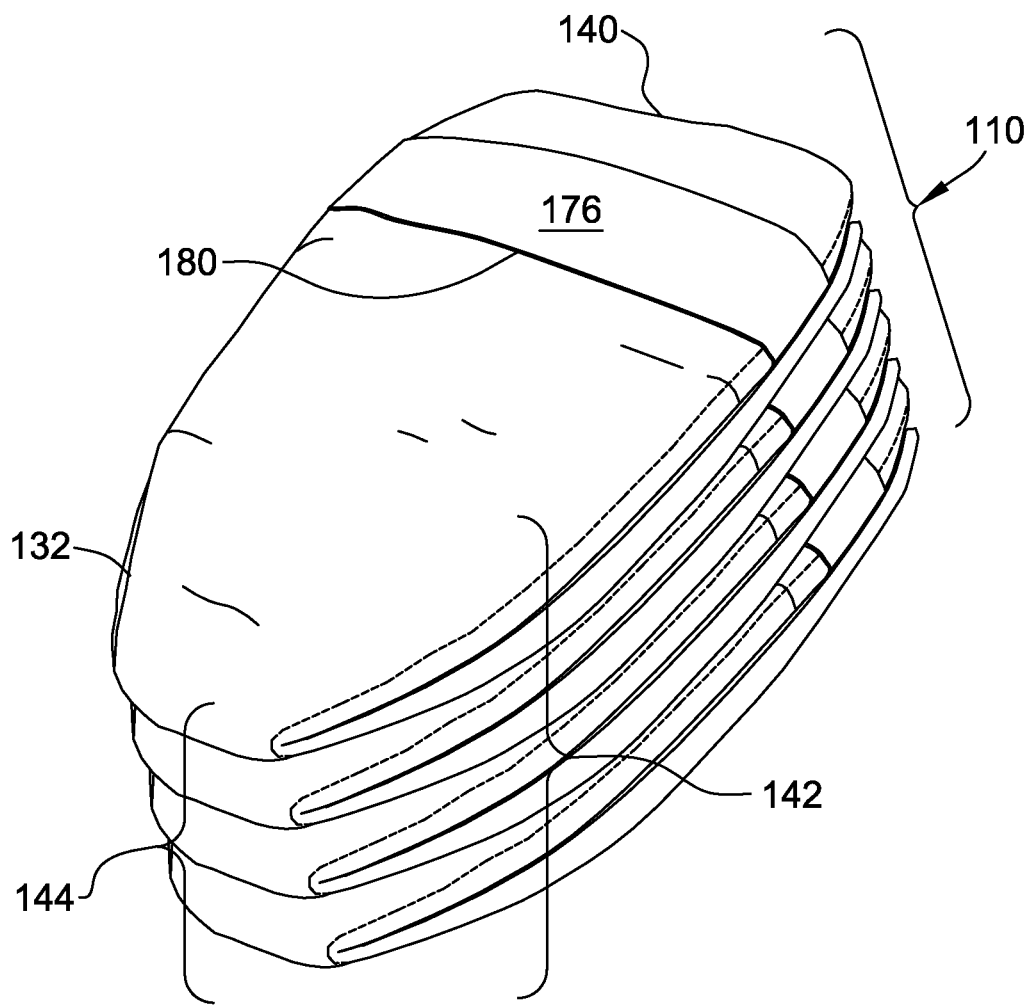
FIG. 11 is a perspective view of a plurality of stacked diapers of FIG. 4 with each diaper in the stack being in the folded state illustrated in FIG. 10.

At the fifth folding step 194, the diaper 110 is folded at or near a lateral fold line 144 such that the back waist edge 138 is generally aligned with the front waist edge 140 in the folded state (as depicted in FIG. 10). In such a folded state, the diaper 110 is well suited for packaging as is well known in the art. For example, the folded diaper 110 may be stacked with like folded diapers (as depicted in FIG. 11) and provided in consumer packaging for retail sale.

Figure 8B:
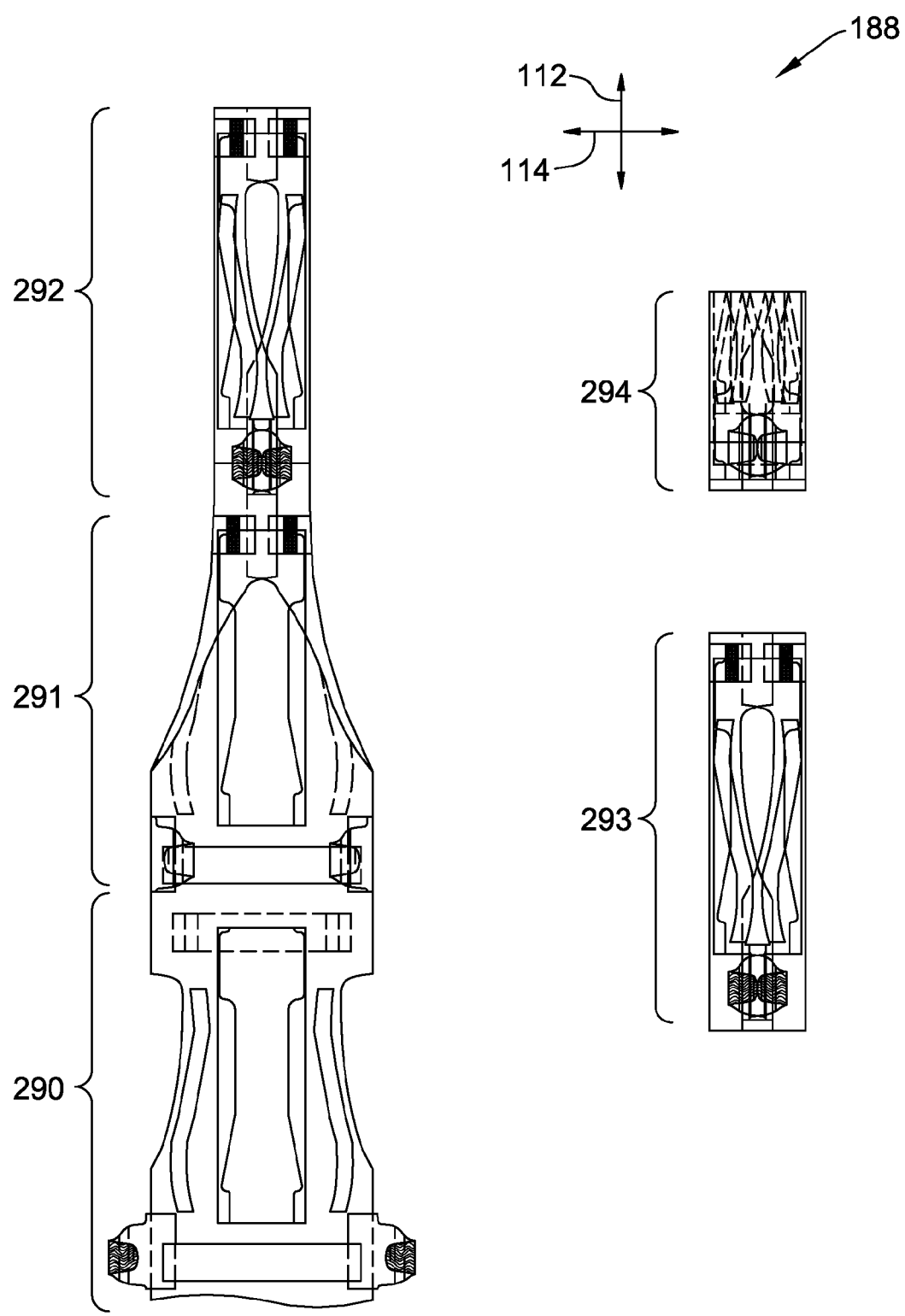
FIG. 8B is a schematic illustrating another suitable folding process of the diaper of FIG. 4.

FIG. 8B illustrates another suitable folding process for the diaper 110. The depicted folding process of FIG. 8B comprises a series of folding steps 290-294 to move the diaper 110 from a substantially flat configuration (as depicted in FIGS. 4 and 5) to a folded configuration (as depicted in FIG. 10). In the first folding step 290, the back ears 122 are folded over on themselves, similar to the first step 190 of the folding process depicted in FIG. 8A. More particularly, in the first folding step 290 the outermost portions of the back ears 122 (i.e., portions of the back ears comprising the grip regions 168 and at least part of the primary first fastening components 124) are folded toward the bodyside liner 130. In some embodiments, the portion of each back ear 122 folded over in step 290 may engage another portion of corresponding the back ear which is not folded over. For example, in some embodiments at least part of the primary first fastening component 124 of each back ear 122 when folded over may engage a part of the elastomeric region 150, the non-elastomeric region 152, and/or the secondary second fastening component 178 provided at each back ear. In one suitable embodiment, the entire primary first fastening component 124 of each back ear 122 is folded over and engaged with the secondary second fastening component 178 of the same back ear.

In the second folding step 291, the folded over back ears 122 are folded towards the outer cover 132 of the diaper 110 (i.e., the folded over ears away from the view depicted in FIG. 8B generally at a location of the longitudinal side edges 128). At such a step, portions of the folded over back ears 122 may overlap portions of the outer cover 132. Thus, unlike a position of the back ears 122 following the second folding step 191 of the folding process depicted in FIG. 8A, following the second folding step 291 the back ears will be folded against the outer cover 132 of the diaper 110.

Also at the second folding step 291, the front portion 116 of the diaper 110 is folded such that the longitudinal edges of the front portion overlap one another near a center line 198 of the diaper in a substantially similar manner as in folding step 191.

In the third folding step 292, the back portion 118 of the diaper is folded over in a similar manner to the front portion 116 as folded in step 291. More particularly, a first of the two longitudinal edges 128 at the back portion 118 of the diaper 110 is first folded toward the bodyside liner 130 of the diaper 110 such that the first longitudinal edge extends past the center line 198 of the diaper, with the second of the two longitudinal edges then folded over in a similar manner to form the overlap region 196 near the center line 198 of the diaper where a rightmost and leftmost portion of the back portion 118 of the diaper overlap one another (as viewed in FIG. 9B).

As seen in FIG. 8B, at the fourth folding step 293, the diaper 110 is removed from the length of absorbent articles 188 by, e.g., cutting the diaper along the back waist edge 138 of the leading diaper and the front waist edge 140 of the trailing diaper. As with the folding process depicted in FIG. 8A, the diaper 110 may be cut from the length of absorbent articles 188 at step 193 by any suitable means well known in the art.

At the fifth folding step 294, the diaper 110 is folded at or near a lateral fold line 144 such that the back waist edge 138 is generally aligned with the front waist edge 140 in the folded state (as depicted in FIG. 10). In such a folded state, the diaper 110 is well suited for packaging as is well known in the art. For example, the folded diaper 110 may be stacked with like folded diapers (as depicted in FIG. 11) and provided in consumer packaging for retail sale.

In one suitable embodiment, the folded and stacked diapers 110 (following, e.g., either suitable folding process described above) can be placed into suitable flexible packaging to define a compressed package. By "compressed package" it is meant a package that contains a plurality of diapers 110 wherein the plurality of diapers have a pre-insertion dimension, measured along at least one axis, which is greater in length than when the plurality of diapers are contained in the packaging. For example, if fourteen diapers 110 are assembled into a row having a pre-insertion dimension, measured along an axis, e.g., the x axis, of 10 inches (254 mm) and the row of diapers are then compressed by a force of at least 1 pound to a dimension of less than 10 inches (254 mm) when they are contained in the packaging, then the articles are considered to be contained in a compressed package. More specifically, the diapers 110 can be compressed and inserted into the packaging. After the diapers 110 are placed in the packaging, the packaging is sealed. The compressed diapers 110 try to expand from their compressed configuration to an uncompressed configuration within the sealed packaging. The cumulative expansion efforts of the diapers 110 place the packaging under tension. Suitably, the compressed diapers 110 apply between about 1 pound and about 20 pounds of force against the packaging (i.e., an in-bag force), and more suitably between about 7 pounds and about 12 pounds. In one suitable embodiment, the diapers 110 apply about 9 pounds of force against the packaging 11.

As a result of such a folding process depicted in FIG. 8A, the secondary first fastening components 126 will be disposed on an inside of the folded diaper 110 as illustrated in FIG. 10. Thus, the secondary first fastening components 126 are not prone to engaging other objects and/or diapers 110 during manufacturing and/or packaging of the diaper. Further, when provided in a stack of similar diapers (as depicted in FIG. 11) the diaper 110 will not engage an adjoining diaper. Thus, a user of the diaper 110 may easily remove the diaper from a package or the like without having to forcibly separate the diaper from an adjoining diaper. Thus may reduce, e.g., the delamination or tearing of the outside cover 132 of one or more of the stacked diapers 110.

Figure 9A:
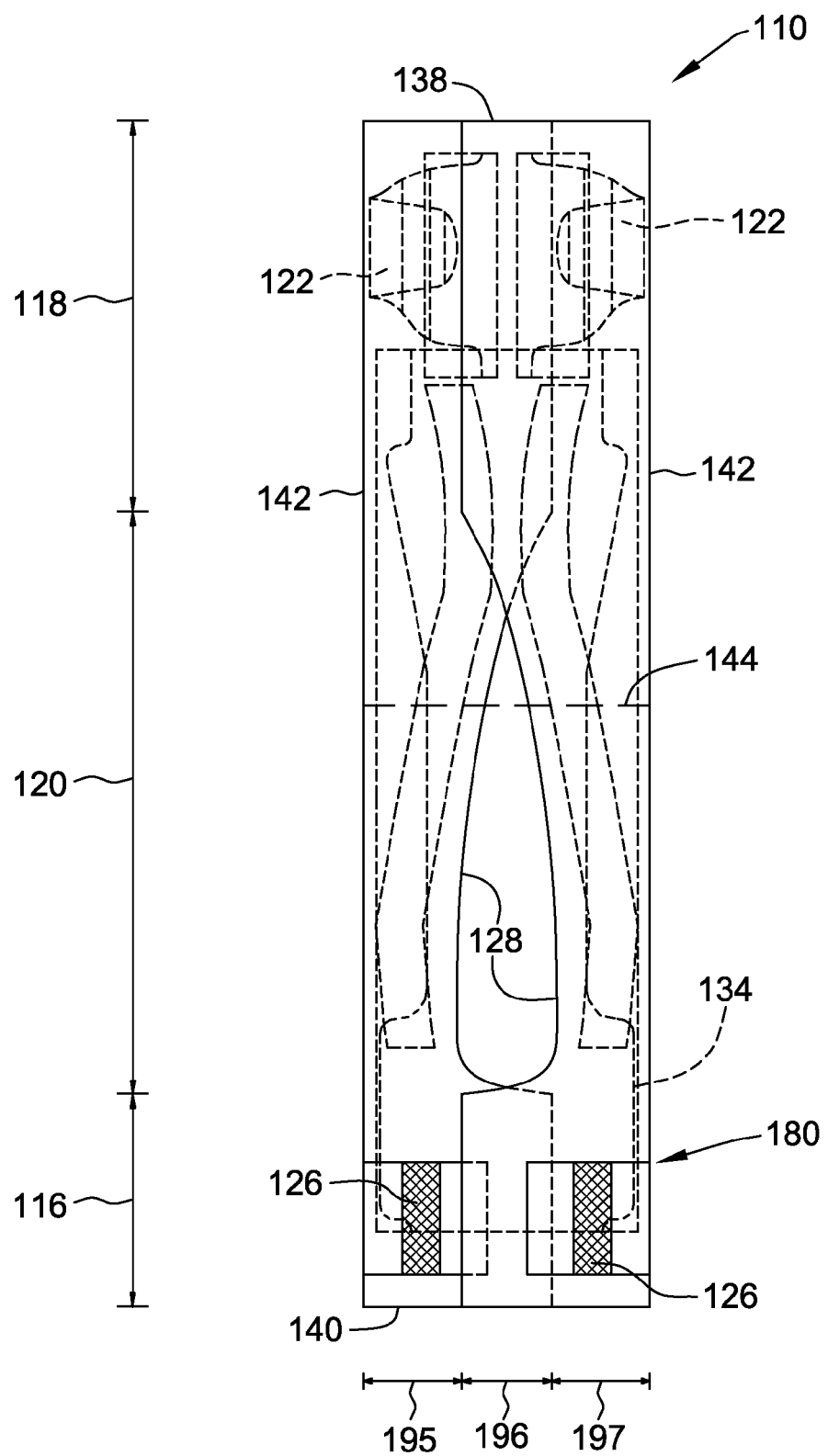
FIG. 9A is the diaper of FIG. 4 tri-folded according to the folding process of FIG. 8A.
Figure 9B:
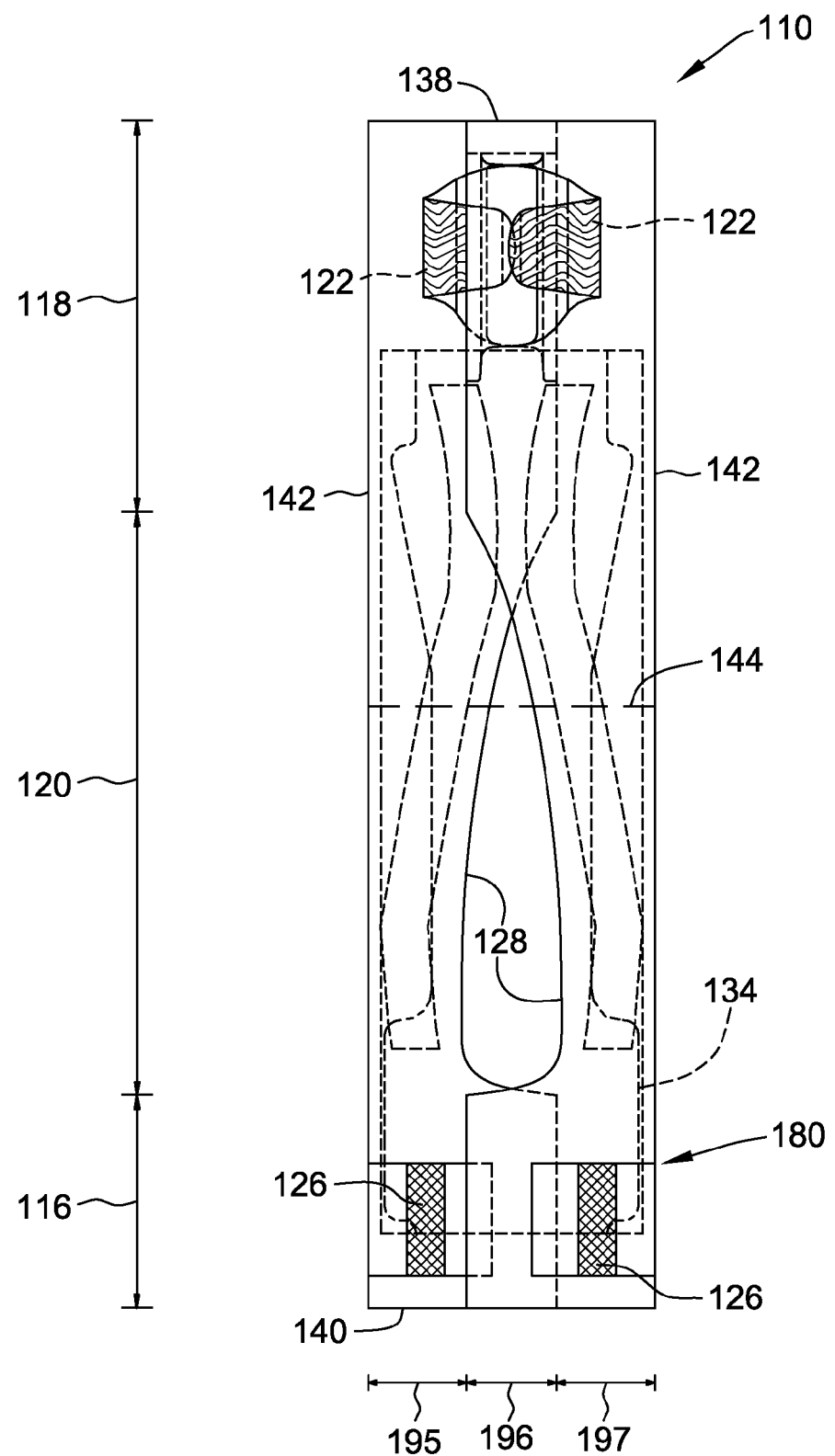
FIG. 9B is the diaper of FIG. 4 tri-folded according to the folding process of FIG. 8B.

Further, and because each secondary first fastening component 126 is offset a sufficient distance from a corresponding longitudinal side edge 128, the secondary first fastening components will not engage the bodyside liner 130 when the diaper 110 is in the folded configuration. This may be more readily understood with reference to FIGS. 9A and 9B. FIG. 9A illustrates the diaper 110 at, e.g., the fourth folding step 193 as discussed in connection with FIG. 8A. FIG. 9B illustrates the diaper 110 at, e.g., the fourth folding step 293 as discussed in connection with FIG. 8B. Following the fourth folding steps 193, 293 the right longitudinal side edge 128 of the diaper 110 will overlap the left longitudinal side edge 128 near the front portion 116 forming the overlap region 196 (as viewed in FIGS. 9A and 9B). It will be appreciated that in other embodiments the left longitudinal side edge 128 may overlap the right longitudinal side edge 128 to form the overlap region 196 without departing from the scope of this disclosure.

Each secondary first fastening component 126 is spaced a sufficient distance from a corresponding longitudinal side edge 128 such that neither secondary first fastening component is located in the overlap region 196 following the fourth folding steps 193, 293. Accordingly, when the diaper 110 is further folded in the fifth folding steps 194, 294 (i.e., folded along lateral fold line 144 to the folded configuration depicted in FIG. 10), neither secondary first fastening component 126 will engage the bodyside liner 130 of the diaper. Rather, when the diaper 110 is folded about lateral fold line 144 such that the front waist edge 140 is generally aligned with the back waist edge 138, both secondary first fastening components 126 will engage the outer cover 132 of the diaper (if folded according to the embodiment depicted in FIG. 8A) or the back ears 122 (if folded according to the embodiment depicted in FIG. 8B).

More particularly, if folded according to the process depicted in FIG. 8A, the rightmost secondary first fastening component 126 disposed in the right region 197 will engage a portion of the outer cover 132 in the back portion 118 of the diaper 110 located in the right region (as viewed in the accompanying Figures), and the leftmost secondary first fastening component provided in the left region 195 will engage a portion of the outer cover in the back portion of the diaper located in the left region. If folded according to the process depicted in FIG. 8B, the rightmost secondary first fastening component 126 disposed in the right region 197 will engage a portion of the back ear 122 located in the right region, and the leftmost secondary first fastening component provided in the left region 195 will engage a portion of the back ear located in the left region.

Disposing each secondary first fastening component 126 at a position such that it is located inside of the folded diaper 110 (as depicted in FIG. 10) and such that it is not located in the overlap region 196 provides a number of benefits. First, because the secondary first fastening components 126 are provided on an inside of the folded diaper 110, they will not engage with other objects and/or other diapers during manufacturing, packaging, and/or use of the diaper. Thus, the diaper 110 may be easily packaged in a stack of diapers (as illustrated in FIG. 11) without each diaper engaging one or more adjoining diapers, preventing machine downtime or waste. Further, this may reduce or even eliminate inadvertent tearing, delamination, etc., of adjoining diapers when a diaper 110 is ultimately removed from the stack for use.

Further, and because the secondary first fastening components 126 may be disposed outboard of the overlap region 196 following the fourth folding step 193 in some embodiments (i.e., the rightmost secondary first fastening component is disposed in the right region 197 and the leftmost secondary first fastening component is disposed in the left region 195) the secondary first fastening components will preferably not engage the bodyside liner 130 and/or a containment flap (not shown) of the diaper 110 when the diaper is in the folded configuration (FIG. 10). Thus, when the diaper 110 is ultimately unfolded for use, the secondary first fastening components 126 will not, e.g., tear the bodyside liner 130 or the flap. This prevents residual portions of the bodyside liner 130 or flap from remaining on the secondary first fastening components 126, which would decrease the overall effectiveness of the secondary fastening system, as well as keeps the bodyside liner and flap intact to reduce leakage while preserving the aesthetic appeal of the diaper 110 to a user.

Still further, and again because the secondary first fastening components 126 may preferably be provided in the outboard regions (i.e., left region 195 and right region 197) of the overlap region 196 following the fourth folding step 193, both secondary first fastening components will engage the outer cover 132 or the back ears 122 when the diaper 110 is folded along lateral fold line 144 in the fifth folding step 194. Thus, the diaper 110 will be more readily kept in the folded state (FIG. 10) until use.

In some embodiments, the folded and stacked diapers 110 may be placed into suitable flexible packaging to define a compressed package (as discussed). In such embodiments, the tension which the folded and stacked diapers 110 applies against the packaging (i.e., the in-bag force) may facilitate the engagement of the secondary first fastening components 126 with the outer cover 132. More particularly, the in-bag force may compress the secondary first fastening components 126 against the outer cover 132 such that most or all of the surface area of the secondary first fastening components engage the outer cover. In such embodiments, the folded diaper 110 may more readily remain in the folded configuration once removed from the packaging, etc., due to the engagement of the secondary first fastening components 126 with the outer cover 132.

Figure 12:
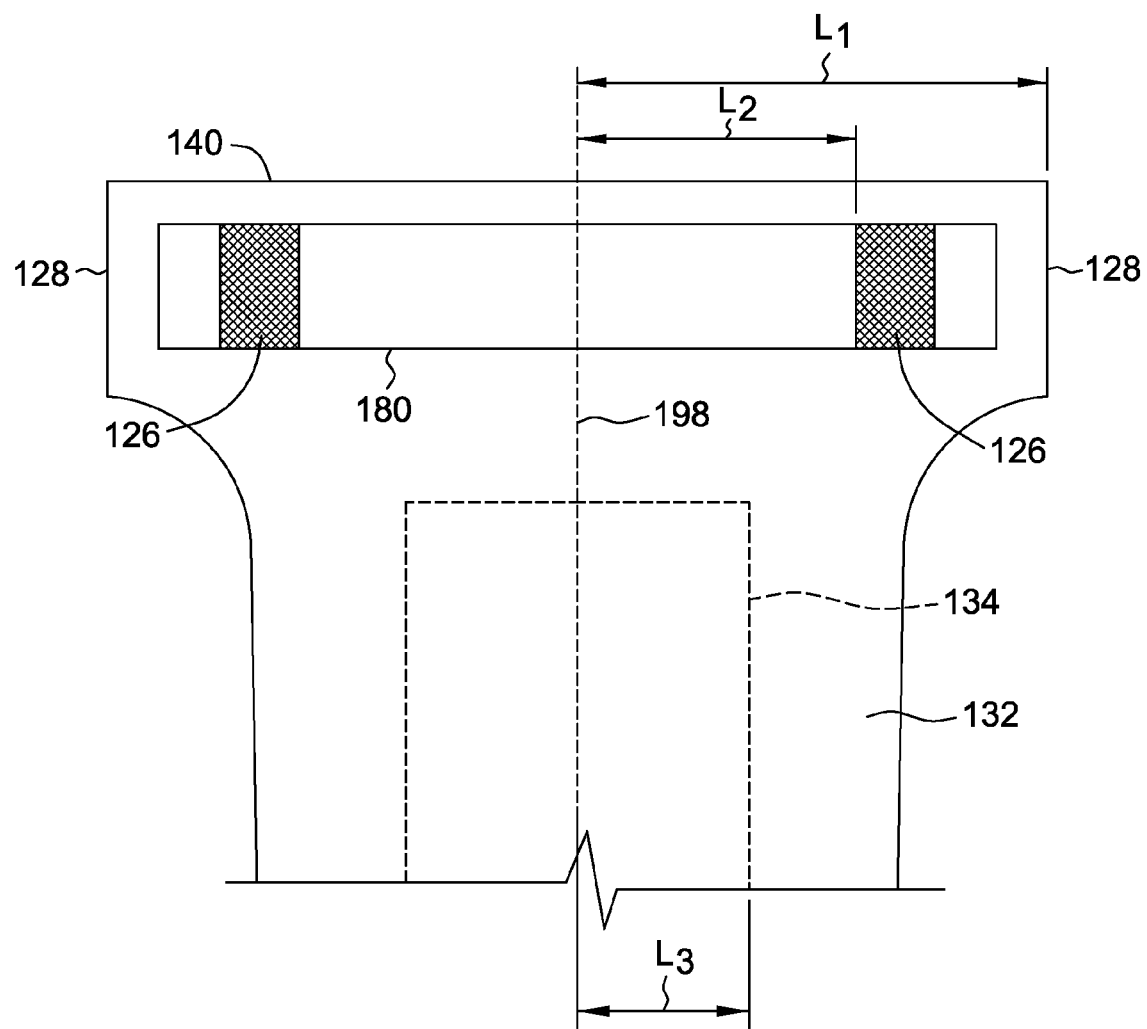
FIG. 12 is a top plan view of a portion of the diaper of FIG. 4 illustrating relative distances from a center line to various components of the diaper.

One suitable placement of the secondary first fastening components 126 in relation to other components of the diaper 110 in order to achieve one or more of the described benefits may be more readily understood with reference to FIG. 12. FIG. 12 is a schematic of a portion of the diaper 110 depicted in FIG. 4 with relative dimensions between the components labeled L1, L2, and L3 for convenience. For example, L1 indicates a distance of the outer edge 128 of the front portion 116 from a center line 198 which is coaxially aligned with the longitudinal axis of the diaper 110; L2 indicates a distance of an inboard edge of one of the secondary first fastening components 126 from the center line; and L3 indicates a narrowest lateral distance of a longitudinally extending edge of the absorbent core 134 located in the front portion of the diaper from the center line.

In some embodiments, a ratio of L2:L1, L2:L3, and/or L1:L3 may be appropriately configured such that the diaper 110 exhibits one or more benefits described. For example, in some embodiments the ratio of L2:L1 and L2:L3 may be appropriately configured so, when folded, the secondary first fastening components 126 are provided on an inside of the diaper 110 and outboard of the overlap region 196 such that the secondary first fastening components are not externally exposed and such that the secondary first fastening components engage the outer cover 132 or the back ears 122 (and not a bodyside liner 130) of the folded diaper.

For example, in some embodiments, the diaper may be constructed such that the ratio of L2:L1 (i.e., the ratio of a distance from the center line 198 to an inboard edge of the secondary first fastening component 126 compared to a distance from the center line to the outer edge 128 of the front portion 116 of the diaper 110) is at least 0.50 and is less than 1.00. Preferably, the diaper 110 may be constructed such that the ratio of L2:L1 is between 0.50 and 0.80, and more preferably between 0.50 and 0.70, and even more preferably between 0.50 and 0.65.

Further, in some embodiments, the diaper 110 may be constructed such that the ratio of L2:L3 (i.e., the ratio of the distance from the center line 198 to the inboard edge of the secondary first fastening component 126 compared to a distance from the center line to an outer edge of the absorbent core 134) is greater than 1.15. Preferably, the diaper 110 may be constructed such that the ratio of L2:L3 is between 1.15 and 1.80, and more preferably between 1.15 and 1.70, and even more preferably between 1.15 and 1.60.

Figure 13B:
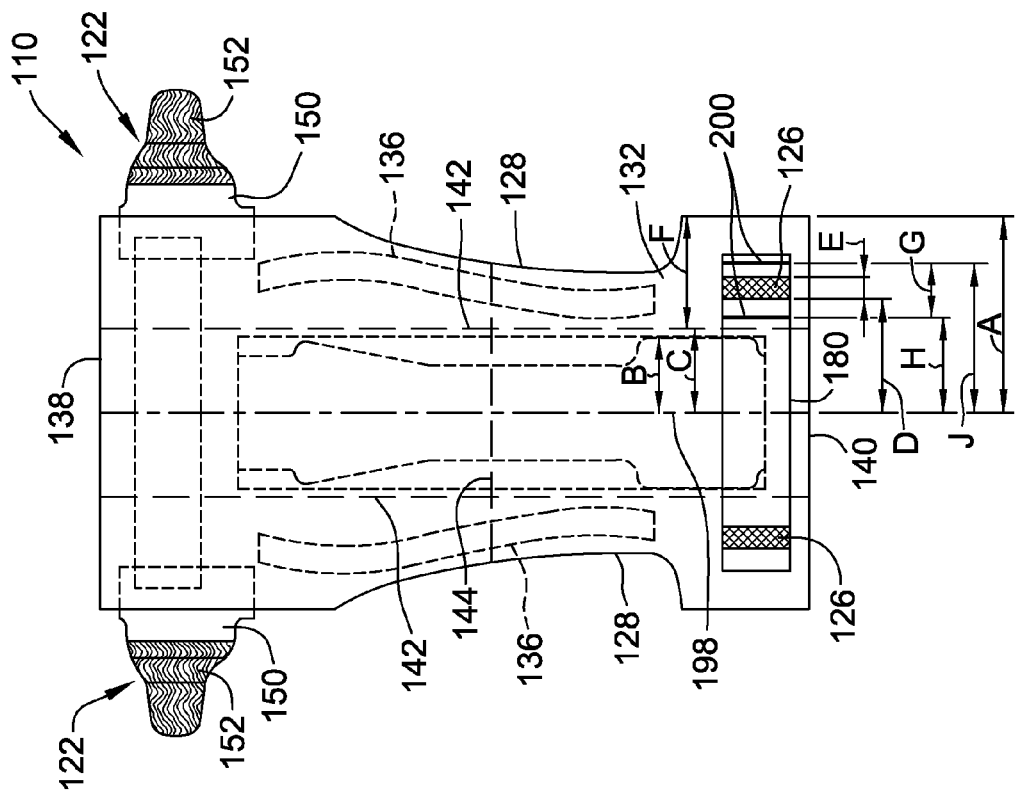
FIG. 13B is a top plan view of the unfolded diaper of FIG. 4, and FIGS. 13C-13E are cross-sectional views of various embodiments of the diaper tri-folded, with each figure illustrating relative distances from a center line to various components of the diaper.
Figure 13A:
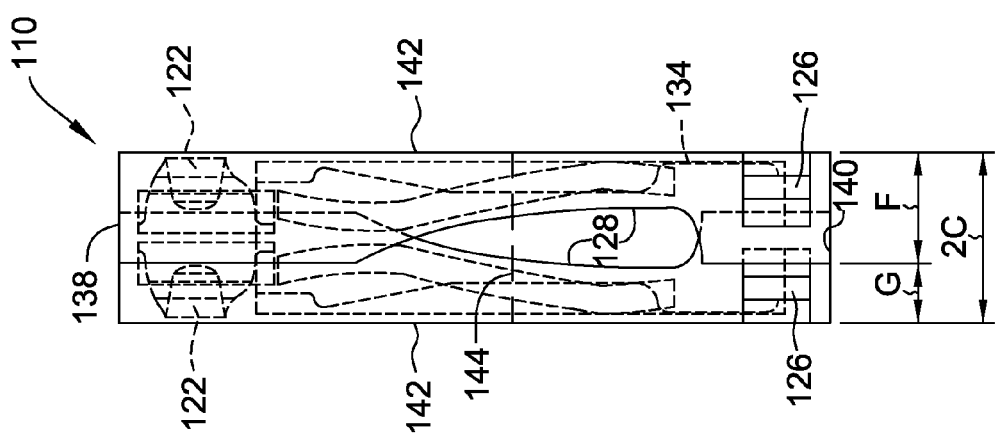
FIG. 13A is the diaper of FIG. 4 tri-folded in a similar manner as depicted in FIG. 9A.

Another suitable placement of the secondary first fastening components 126 in relation to other components of the diaper 110 in order to achieve one or more of the described benefits may be more readily understood with reference to FIGS. 13A and 13B. FIGS. 13A and 13B depict bolded lines 200 which indicate an appropriate range on the front portion 116 of the diaper 110 in which to dispose the secondary first fastening components 126 according to some embodiments such that they exhibit one or more of the benefits described. Although the bolded lines 200 are only depicted on the right side of the front portion 116 of the diaper 110 in FIG. 13B, one skilled in the art will appreciate that the diaper may be symmetrical about its center line 198 such that the secondary first fastening component 126 disposed on the left side of the front portion of the diaper will be disposed in a substantially similar range from the center line 198.

As shown in FIGS. 13A and 13B, an appropriate lateral region, G, to position an inboard-most longitudinal side of the secondary first fastening component 126 may be defined in relation to a distance from the center line 198 to the side edge 128 at the front portion 116, A, a distance from the center line to the longitudinal edge of the absorbent core 134, B, a distance from the center line to the longitudinal fold line 142, C, a distance from the center line to the inboard longitudinal edge of the secondary first fastening component, D, a width of the secondary first fastening component, E, and/or a distance from the longitudinal fold line to the side edge at the front portion, F.

For example, in some embodiments the diaper 110 may be constructed such that an inner region boundary, H (i.e., an inboard side of the lateral region G) is disposed from the center line 198 a distance equal to the distance from the center line 198 to the longitudinal fold line 142, C, plus 6 millimeters (i.e., H=C+6 mm). Further, the lateral region, G, may be defined as having a width equal to two times the distance from the center line 198 to the longitudinal fold line 142, C, less the distance from the longitudinal fold line to the side edge 128 at the front portion 116, F, less 6 millimeters (i.e., G=2*C−F−6 mm). Accordingly, the diaper 110 may be constructed such that the outer region boundary, J (i.e., an outboard side of the lateral region, G) is disposed from the center line 198 a distance equal to the distance from the center line 198 to the longitudinal fold line 142 plus 6 millimeters, H, plus the width of the lateral region, G (i.e., J=H+G). In embodiments where the distance from the center line 198 to the longitudinal fold line 142 plus 6 millimeters, H, plus the width of the lateral region, G, is greater than the distance from the center line to the side edge 128 at the front portion 116, A, less 6 millimeters, the outer region boundary, J, may alternatively be defined as the distance from the center line to the side edge at the front portion, A, less 6 millimeters (i.e., J=A−6 mm).

In other suitable embodiments, the inner region boundary, H (i.e., an inboard side of the lateral region G) may be defined according to a relative location of the longitudinal fold lines 142 to the longitudinally extending center line 198. For example, in embodiments where the longitudinal fold lines 142 are disposed very near or even within the absorbent core 134, a inboard-most longitudinal edge of the secondary first fastening components 126 may need to be spaced further outboard so that the secondary first fasteners will be folded within the diaper 110 than in embodiments where the longitudinal fold lines are spaced farther apart from the absorbent core. That is, because the absorbent core 134 may have a non-negligible thickness, in embodiments where the longitudinal foldlines 142 are very near or within the absorbent core, when the diaper 110 is folded along the longitudinal fold lines the diaper wraps around the thickness of the absorbent core. Thus, the secondary first fastening components 126 may need to be spaced from the longitudinal fold lines 142 a distance equal to the thickness of the absorbent core 134 plus a predetermined process range to ensure the secondary first fastener is sufficiently included within the folded diaper 110. However, when the longitudinal fold lines 142 are spaced farther away from the absorbent core 134, the diaper 110 does not wrap around the thickness of the absorbent core at a location of the fold lines, and thus the inboard-most edge of the secondary first fastening components 126 may be disposed nearer the fold lines and still be entirely disposed within the diaper in the folded state.

Figure 13C:
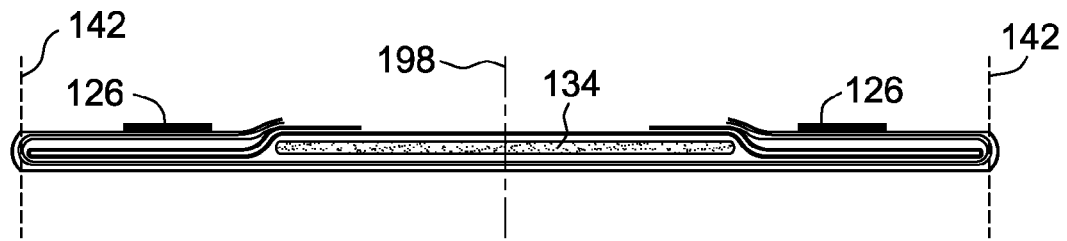
Figure 13D:
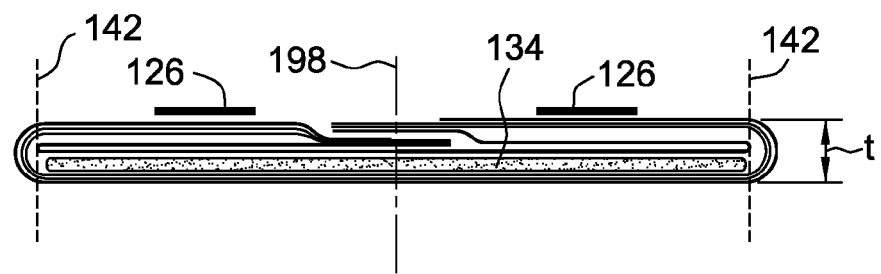
Figure 13E:
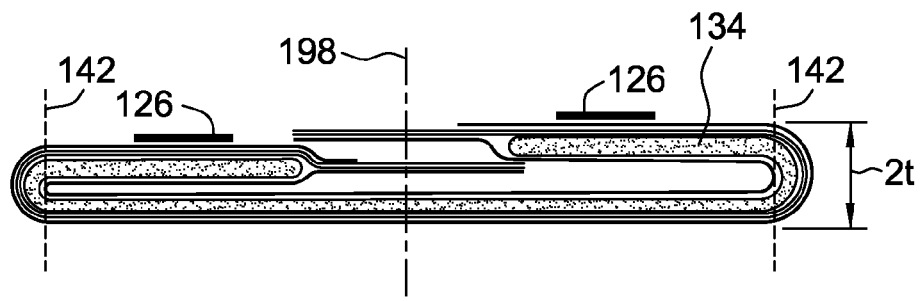

This may be more readily understood with reference to FIGS. 13C-13E. First, FIG. 13C illustrates a cross-sectional view of the diaper 110 wherein the longitudinal fold lines 142 are spaced sufficiently far away from the absorbent core 134, such that a thickness of the absorbent core will not affect or only negligibly affect a location of the secondary first fastening components in the folded configuration. Specifically, the longitudinal fold lines 142 are sufficiently spaced from the center line 198 such that, when the diaper 110 is folded, the diaper does not have to "wrap around" the absorbent core 134. In such embodiments, the inner region boundary, H, of the lateral region, G, may be configured such that an inboard longitudinal edge of the secondary first fastening components 126 (i.e., the outboard most edges of each in the folded state) are disposed no closer to the center line than a predetermined process range distance from the longitudinal fold lines. That is, the inner region boundary, H, may be defined as the distance from the center line 198 to the longitudinal fold line, C, plus a predetermined process range, PR (i.e., H=C+PR). Preferably, the predetermined process range is about six millimeters.

However, when the fold lines 142 are disposed nearer the absorbent core 134, as depicted in FIG. 13D, the diaper 110 will need to "wrap around" the edges of the absorbent core when folded. Thus, in order to space the secondary first fasteners 126 a same distance from the folded edge of the diaper 110 as in, e.g., FIG. 13C, a thickness of the absorbent core, t, must be taken into account when calculating the inner region boundary, H. Thus, in such embodiments, the inner region boundary, H, may be defined as the distance from the center line 198 to the longitudinal fold line, C, plus the thickness of the absorbent core, t (e.g., a dimension of the absorbent core perpendicular to both the longitudinal and lateral directions 112, 114) such that the diaper 110 can sufficiently wrap around the absorbent core, plus the predetermined process range, PR (i.e., H=C+t+PR). Again, the predetermined process range is preferably about six millimeters.

In still other embodiments, and as best viewed in FIG. 13E, the longitudinal fold lines 142 may be disposed within the absorbent core 134. In such configurations, the absorbent core 134 will be folded on itself at the longitudinal fold line 142, such that, in order to space the secondary first fasteners 126 a same distance from the folded edge of the diaper 110 as in, e.g., FIG. 13C, two times the thickness of the absorbent core, t, must be taken into account when calculating the inner region boundary, H. Thus, in such embodiments, the inner region boundary, H, may be defined as the distance from the center line 198 to the longitudinal fold line, C, plus two times the thickness of the absorbent core, t, such that the absorbent core 134 can sufficiently fold on top of itself, plus the predetermined process range, PR (i.e., H=C+2*t+PR). Again, the predetermined process range is preferably about six millimeters.

In any embodiment, the outer region boundary, J (i.e., an outboard side of the lateral region, G) can be defined generally as less than the distance from the center line 198 to the side edge 128 at the front portion 116, A (i.e., J<A). That is, placing the secondary first fasteners 126 at the longitudinal edge 128 of the diaper 110 may, e.g., cause the secondary first fasteners to engage an undesirable location of the folded diaper (as discussed), may cause irritation to a wearer (because, e.g., each fastener may rub against the wearer's leg during wearing of the diaper), and/or may interfere with a bonding of the bodyside liner 130 and the outer cover 132 at a perimeter of the diaper. Thus, the outer region, J, of the lateral distance, G, may be sufficiently spaced apart from the longitudinal side 128 of the diaper 110 (i.e., J<A) such that one or more of these drawbacks may be eliminated. For example, in some embodiments, the outer region, J, may be defined as the distance from the center line 198 to the side edge 128 at the front portion 116, A, less six millimeters (i.e., J=A−6 mm). In other embodiments, the outer region, J, may be defined as the distance from the center line 198 to the side edge 128 at the front portion 116, A, less ten millimeters (i.e., J=A−10 mm). In still other embodiments, the outer region, J, may be defined as the distance from the center line 198 to the side edge 128 at the front portion 116, A, less fifteen millimeters (i.e., J=A−15 mm) or even less twenty millimeters (i.e., J=A−20 mm) or even less twenty-five millimeters (i.e., J=A−25 mm).

In one suitable embodiment, a distance from the center line 198 to the side edge 128 at the front portion 116, A, may preferably be in a range of 100 millimeters to 175 millimeters. Further, inner region boundary, H (i.e., an inboard side of the lateral region G) may be greater than 58.5 mm, and less than 70.5 mm. Preferably, the inner region boundary, H, may be greater than 60.0 mm and less than 65.0 mm, and even more preferably greater than 61.0 mm and less than 62.0 mm.

Further, the outer region boundary, J (i.e., an outboard side of the lateral region, G) may be greater than 81.5 mm and less than 99 mm. Preferably, the outer region boundary, J, may be greater than 85 mm and less than 90 mm, and even more preferably greater than 86 mm and less than 88 mm.

Accordingly, for a given diaper 110 with known dimensions of various components (e.g., a distance from a center line 198 of the diaper to the edge of the absorbent core 134, the longitudinal fold line 142, the edge of the diaper 128, etc.) an appropriate lateral region for positioning the secondary first fastening component 126 may be readily determined. When the secondary first fastening component 126 is disposed in this region (i.e., when disposed in the lateral region, G, as depicted in FIGS. 13A and 13B), the secondary first fastening component may exhibit one or more of the benefits as described herein.

Figure 14:
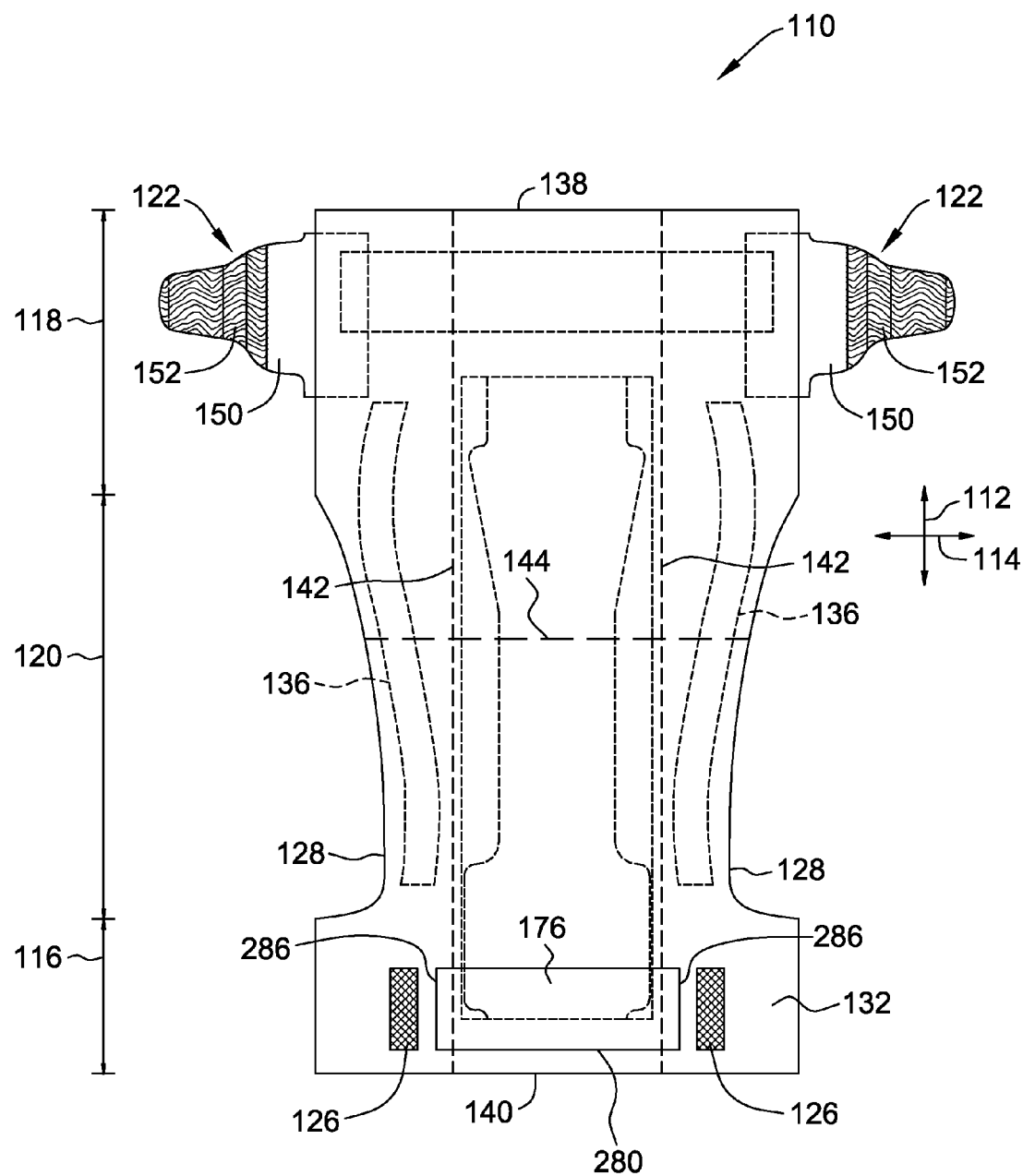
FIG. 14 is a top plan view of a diaper according to another embodiment in an unfolded and laid flat condition to show an outer surface of the diaper which faces away from the wearer when the diaper is worn.

Turning now to FIG. 14, another suitable embodiment of the diaper 110 according to some aspects of the disclosure is illustrated. Specifically, FIG. 14 depicts the diaper 110 in an unfolded and laid flat condition to again show the outer surface of the diaper which faces away from the wearer when the diaper is worn. In the depicted embodiment, the majority of the operable aspects of the diaper 110 are the same or substantially similar to the embodiment depicted in FIGS. 4-9 and as described herein. However, rather than providing secondary first fastening components 126 on the strip 180 as described, in the embodiment depicted in FIG. 14 the pair of secondary first fastening components are disposed directly on the outer cover 132.

More particularly, in the embodiment depicted in FIG. 14, the diaper 110 comprises a strip 280 which includes the primary secondary fastening component 176 and which is shorter in the lateral direction 114 than the strip 180. Unlike the strip 180, the strip 280 does not comprise the secondary first fastening components 126. Rather, the longitudinal edges 286 of the strip 280 are disposed inboard (i.e., closer to the center line 198 of the diaper 110) of the secondary first fastening components 126. Thus, and unlike the embodiment depicted in FIG. 4 where the secondary first fastening components 126 and the strip 180 may be formed as a single unit (e.g., a one piece extruded strip), in this embodiment the secondary first fastening components 126 will be formed separate from the strip 280 and attached directly to the outer cover 132 of the diaper 110.

Figure 15:
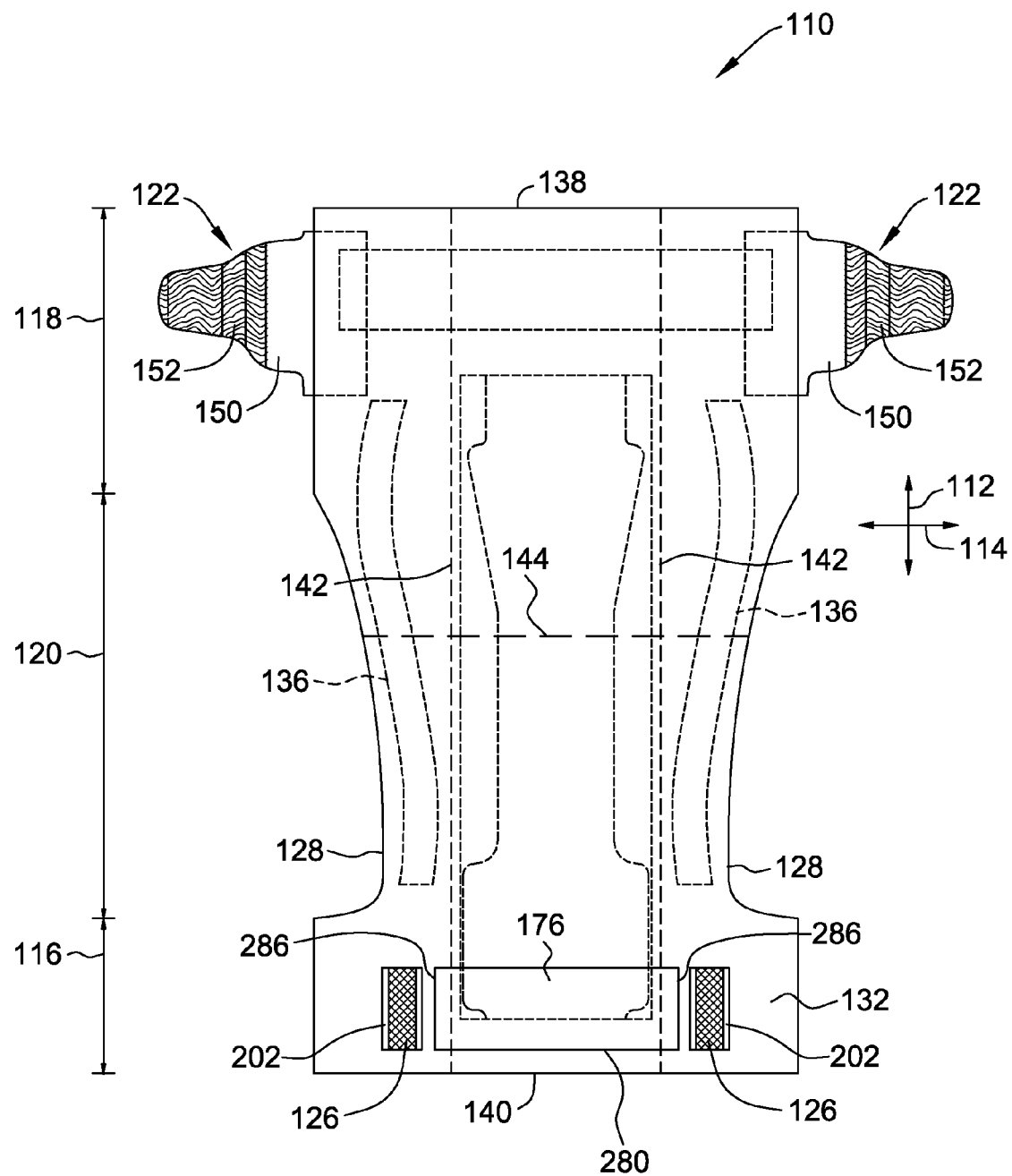
FIG. 15 is a top plan view of a diaper according to still another embodiment in an unfolded and laid flat condition to show an outer surface of the diaper which faces away from the wearer when the diaper is worn.

FIG. 15 illustrates yet another suitable embodiment of the diaper 110 according to some aspects of the disclosure. Again, FIG. 15 depicts the diaper 110 in an unfolded and laid flat condition to show the outer surface of the diaper which faces away from the wearer when the diaper is worn. And again, the majority of the operable aspects of the diaper 110 are the same or substantially similar to the embodiments depicted in FIGS. 4-9 and FIG. 14.

However, in this embodiment, each of the secondary first fastening components 126 are provided on a corresponding carrier 202 which is then attached to or otherwise provided on the outer cover 132. As with the embodiment depicted in FIG. 14, in this embodiment the outer edges 286 of the strip 280 are disposed inboard of the secondary first fastening components 126. However, rather than attaching or otherwise providing the secondary first fastening components 126 directly to the outer cover 132, each secondary first fastening component is intermediately attached to a respective carrier 202 which is then embedded or otherwise attached to the outer cover using any of the discussed methods.

FIG. 16 illustrates yet another suitable embodiment of the diaper 110 according to some aspects of the disclosure. Once again, FIG. 16 depicts the diaper 110 in an unfolded and laid flat condition to show the outer surface of the diaper which faces away from the wearer when the diaper is worn. As with the embodiments depicted in FIG. 14 and FIG. 15, the majority of the operable aspects of the diaper 110 are the same or substantially similar to the embodiments depicted in the FIGS. 4-9.

However, in this embodiment, each of the secondary first fastening components 126 are provided on a corresponding carrier 302 which is then attached to or otherwise provided on the outer cover 132. Further, in this embodiment, outer edges 386 of a strip 380 (which includes primary second fastening component 176) overlap and attach to the carriers 302. That is, the innermost longitudinal edge 304 of each carrier 302 is disposed inboard of a corresponding outer edge 386 of the strip 380. In such embodiments, the carriers 302 may be embedded or otherwise provided to the outer cover 132 of the diaper with the strip 380 overlapping and attached to each of the carriers at a location near the outer edges 386 of the strip.

In one suitable embodiment, the secondary fastening system (and in particular, the secondary first fastening components 126), the back ears 122 (and more particularly, the secondary second fastening component 178), and/or the outer cover 132 of the diaper 110 may be configured such that a peel force (i.e., a force applied by a user or the like of the diaper) needed to disengage the secondary first fastening components from the secondary second fastening components when the diaper is in the wear configuration is much higher than the peel force needed to disengage the secondary first fastening components from the outer cover when the diaper is in the folded configuration. As discussed, when the diaper 110 is provided in the folded configuration, the secondary first fastening components 126 engage the outer cover 132 such that the secondary first fastening components are not exposed to an outside of the diaper and such that the engagement of the secondary first fastening components with the outer cover helps keep the diaper in the folded configuration. However, if the bond between the secondary first fastening components 126 and the outer cover 132 is too great, when the diaper 110 is unfolded for use, the outer cover may tear, delaminate, etc. This may lead to residual pieces of the outer cover 132 remaining on the secondary first fastening components 126 (thus decreasing the effectiveness of the secondary first fastening components) as well as a torn diaper 110 which may leak, provide discomfort to a wearer, and/or which may be aesthetically unappealing to a user.

Accordingly, in some embodiments the components of the diaper 110 are configured such that less peel force is needed to disengage the secondary first fastening components 126 from the outer cover 132 to unfold the diaper than is needed to disengage the secondary first fastening components from the back ears 122 (and more particularly from the secondary second fastening components 178). Thus, during use of the diaper 110, less peel force is required to unfold the diaper for use than is needed to remove the diaper from the wear configuration. The lower peel force needed to unfold the diaper 110 makes the diaper easy to open for use without damaging the diaper while the higher peel force needed to remove the diaper from a wearer ensures the diaper remains securely fastened to the wearer over time notwithstanding the wearer crawling, walking, running, bending, etc.

In some embodiments, this may be accomplished by configuring the secondary first fastening components 126, the secondary second fastening components 178, and/or the outer cover 132 of the diaper 110 to achieve the desired engagement properties. For example, in embodiments where the secondary fastening system is a hook and loop fastening system (i.e., embodiments where the secondary first fastening components 126 comprise hook fasteners and the secondary second fastening components 178 comprise loop fasteners), the loop properties of the outer cover 132 may be reduced such that the bond between the hooks of the secondary first fastening components and the outer cover is less than the bond between the hooks of the secondary first fastening components and the loops of the secondary second fastening components. Further, in embodiments where the secondary fastening system is an adhesive system, the outer cover 132 may be modified to reduce its attachment properties in an area which engages the secondary first fastening components 126 when in the folded state. For example, in some embodiments a release coating may be applied to the outer cover 132 in the area which engages the secondary first fastening components 126 when in the folded state. In other embodiments, a polymer may be selected for the outer cover 132 which comprises the desired attachment properties, and/or one or more polymer additives (such as, e.g., euricimide) may be added to the outer cover 132. Still further, in embodiments where the secondary fastening system is a cohesive system, the outer cover 132 may be coated sparingly (or in some embodiments not at all) with a cohesive in order to lower the engagement between the secondary first fastening components 126 and the outer cover when in the folded configuration.

This may be more readily understood with reference to a particular example. In some embodiments, the secondary first fastening components 126 may be configured such that it is a Velcro® or similar polyethylene hook, the secondary second fastening components 178 may be configured such that it is made of NBL, and the outer cover 132 may be constructed such that it is an online laminated outer cover with diamond on diamond bonded spunbond facing. In such embodiments, less peel force is needed to disengage the secondary first fastening components 126 from the outer cover 132 of the diaper 110 when in the folded configuration than is needed to disengage the secondary first fastening components from the secondary second fastening components 178 when in the wear configuration. Further, in some embodiments less peel force is needed to disengage the secondary first fastening components 126 from the outer cover 132 than fastening components engage the outer cover of known diapers when in the folded configured.

An experiment was conducted (the "Diaper Opening Force Test") to test the peel force needed to disengage the above described configuration of the secondary first fastening components 126 from the outer cover 132 as compared to the peel force needed to disengage known secondary first fastening components from the outer cover of a known diaper (i.e., the KC-Mexico diaper). The KC-Mexico diaper disposes each of the pair of fasteners very near a corresponding longitudinal edge of the absorbent core and a corresponding longitudinal fold line such that part of the pair of fasteners engages the outer cover of the KC-Mexico diaper when in the folded configuration (as discussed). The peel force needed to disengage the novel secondary first fastening components 126 described from the outer cover 132 of the diaper 110 was compared to the peel force needed to disengage the pair of fasteners from the outer cover of the KC-Mexico diaper. The results of the experiment showed that much less force was needed to disengage the secondary first fastening components 126 from the outer cover 132 than was needed to disengage the pair of fasteners from the outer cover of the KC-Mexico diaper, thus resulting in decreased tearing, delamination, etc., of the outer cover of the diaper.

The experiment was conducted using a MTS Sintech® tensile frame (serial no. 1G/040696/099) purchased from MTS System Corporation located at 14000 Technology Drive, Eden Prairie, Minn. (hereinafter "the machine"). The machine was configured with a 100 Newton D72795 load cell and upper and lower jaws one inch wide by three inches long. Each of these components were similarly purchased from MTS System Corporation. Each test specimen was outfitted (as will be more fully discussed) with two lengths of one inch wide Scotch® 234 masking tape manufactured and made commercially available by 3M.

Figure 1:
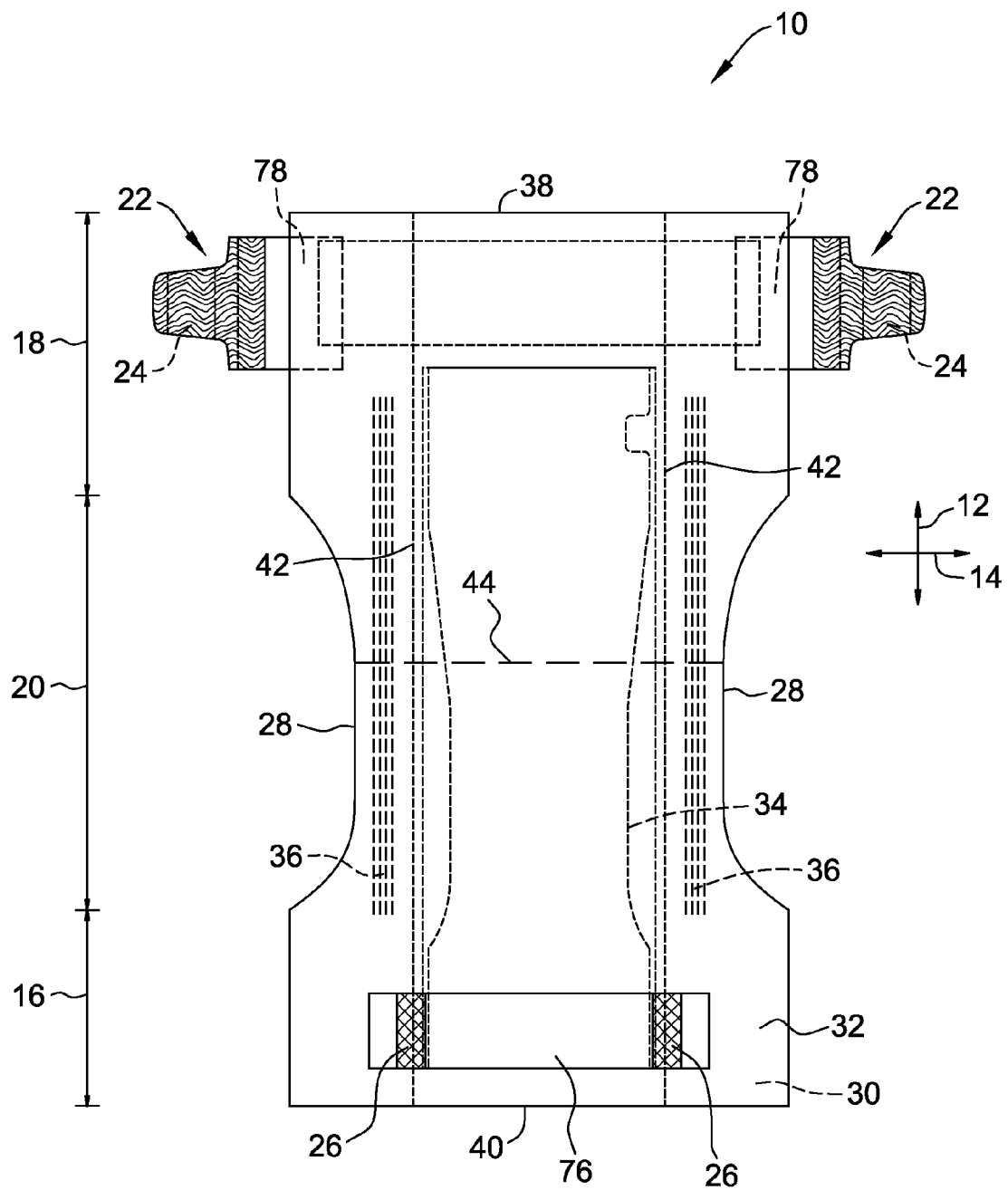
FIG. 1 is a top plan view of a known diaper in an unfolded and laid flat condition to show an outer surface of the diaper which faces away from the wearer when the diaper is worn.
Figure 2:
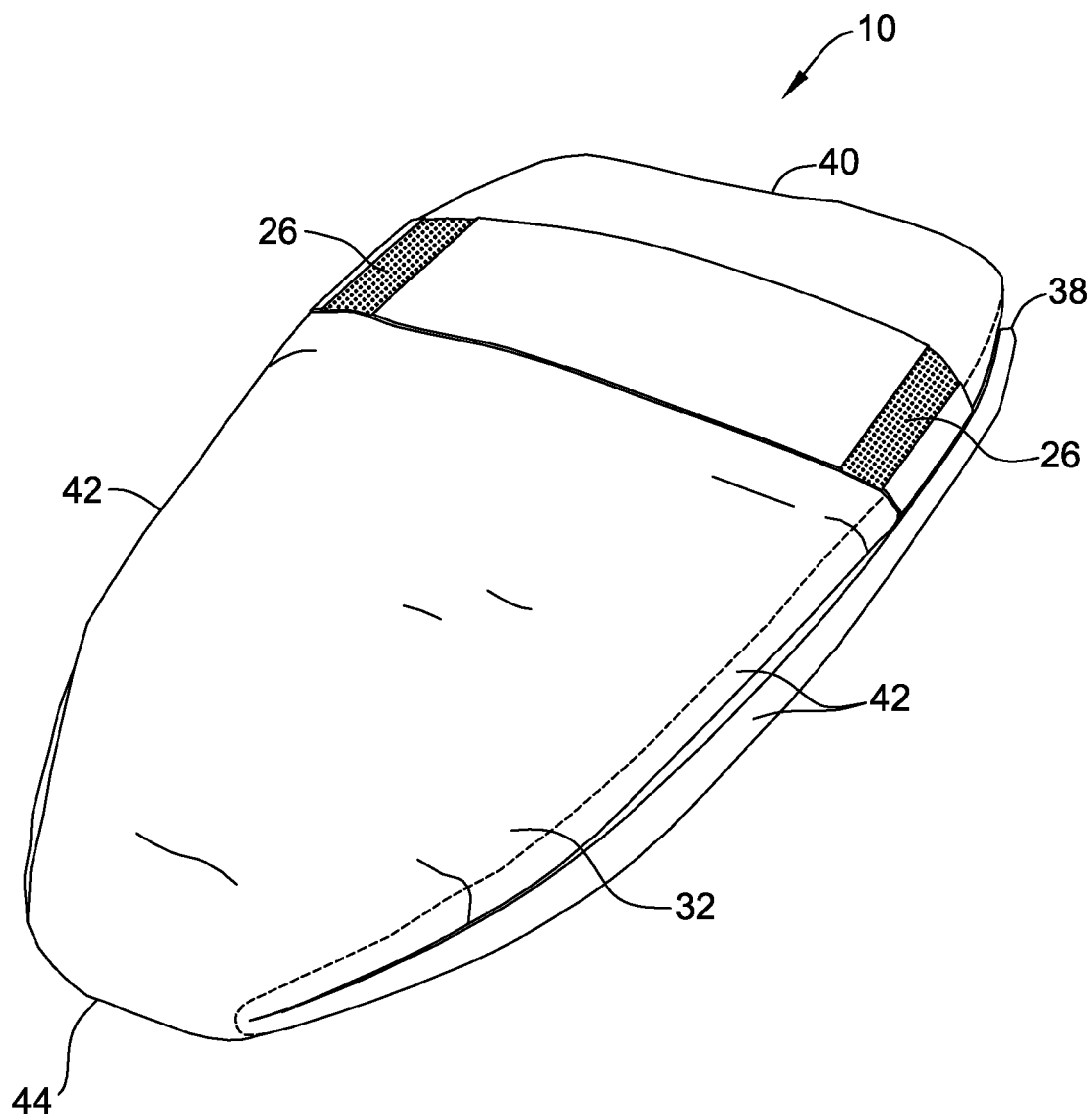
FIG. 2 is a perspective view of the known diaper of FIG. 1 in a folded state.
Figure 3:
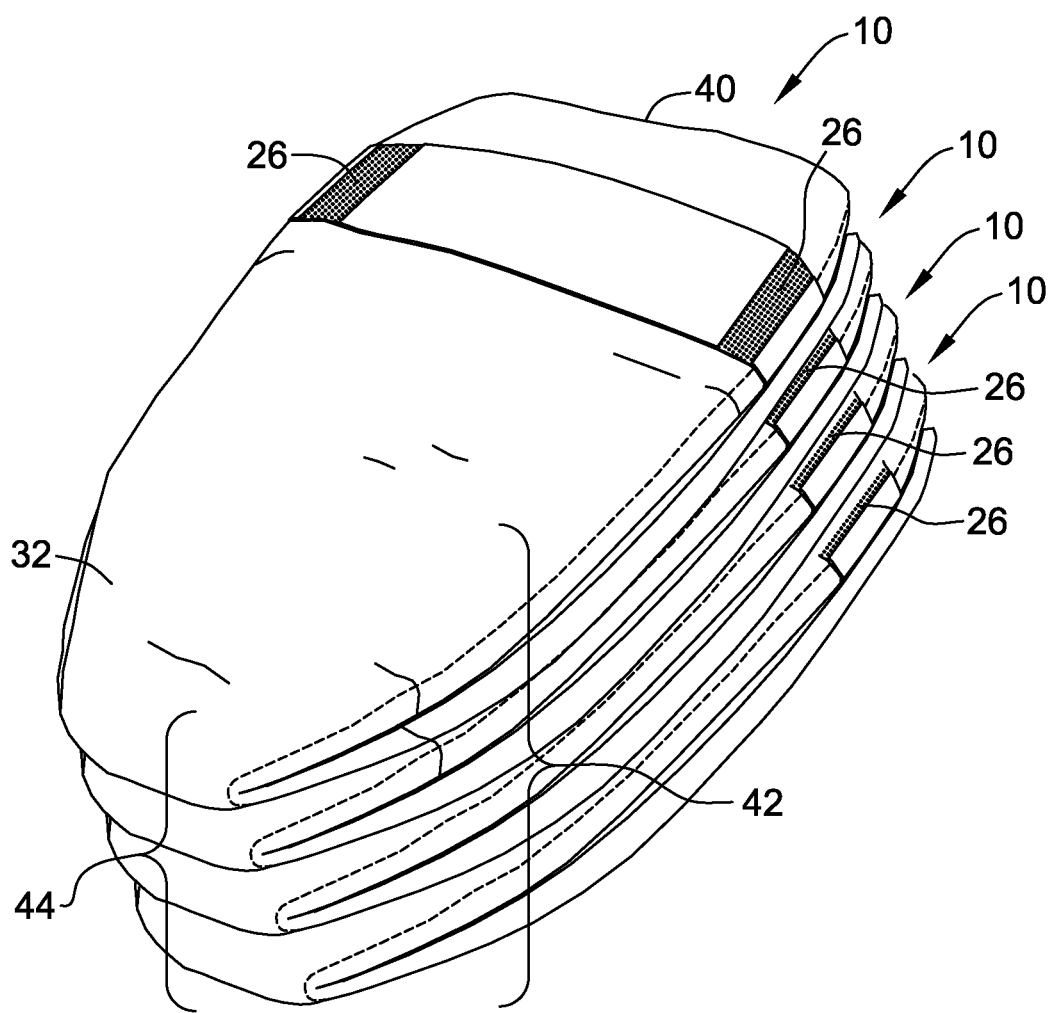
FIG. 3 is a perspective view of a plurality of stacked known diapers of FIG. 1 with each diaper in the stack being in the folded state as illustrated in FIG. 2.
Figure 17:
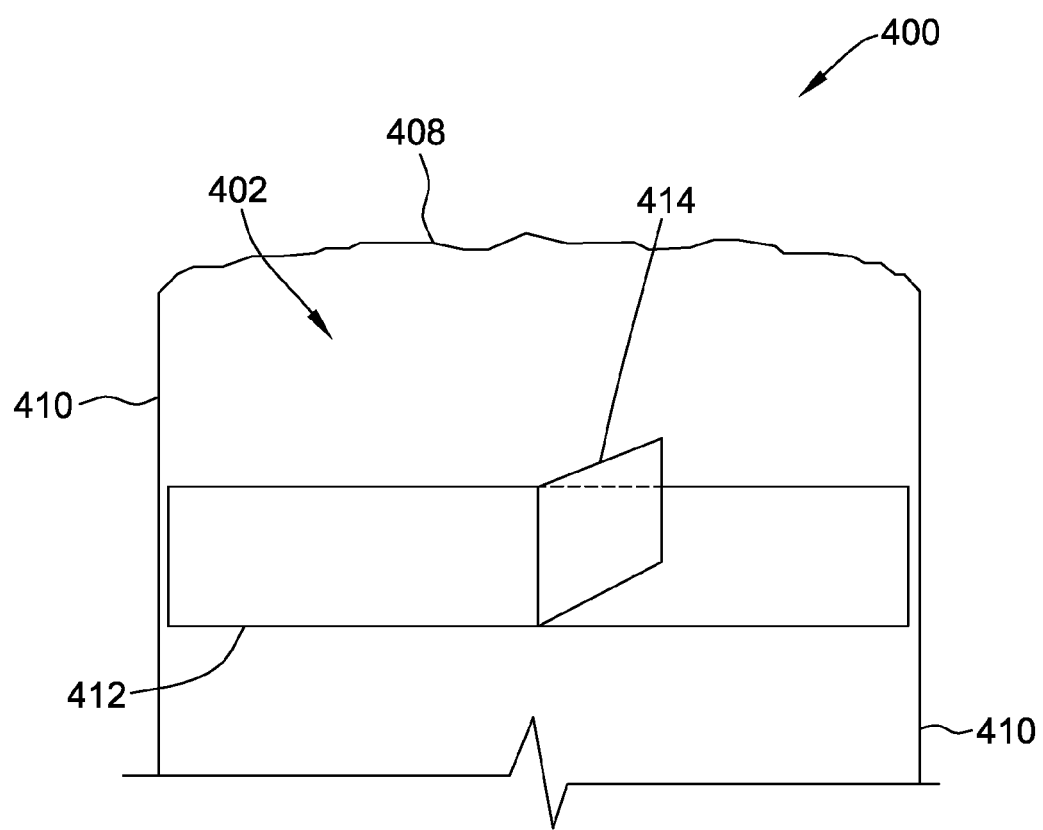
FIG. 17 is a top view of a portion of a folded diaper with a length of masking tape attached thereto for engaging with a testing machine according to some embodiments of the disclosure.
Figure 18:
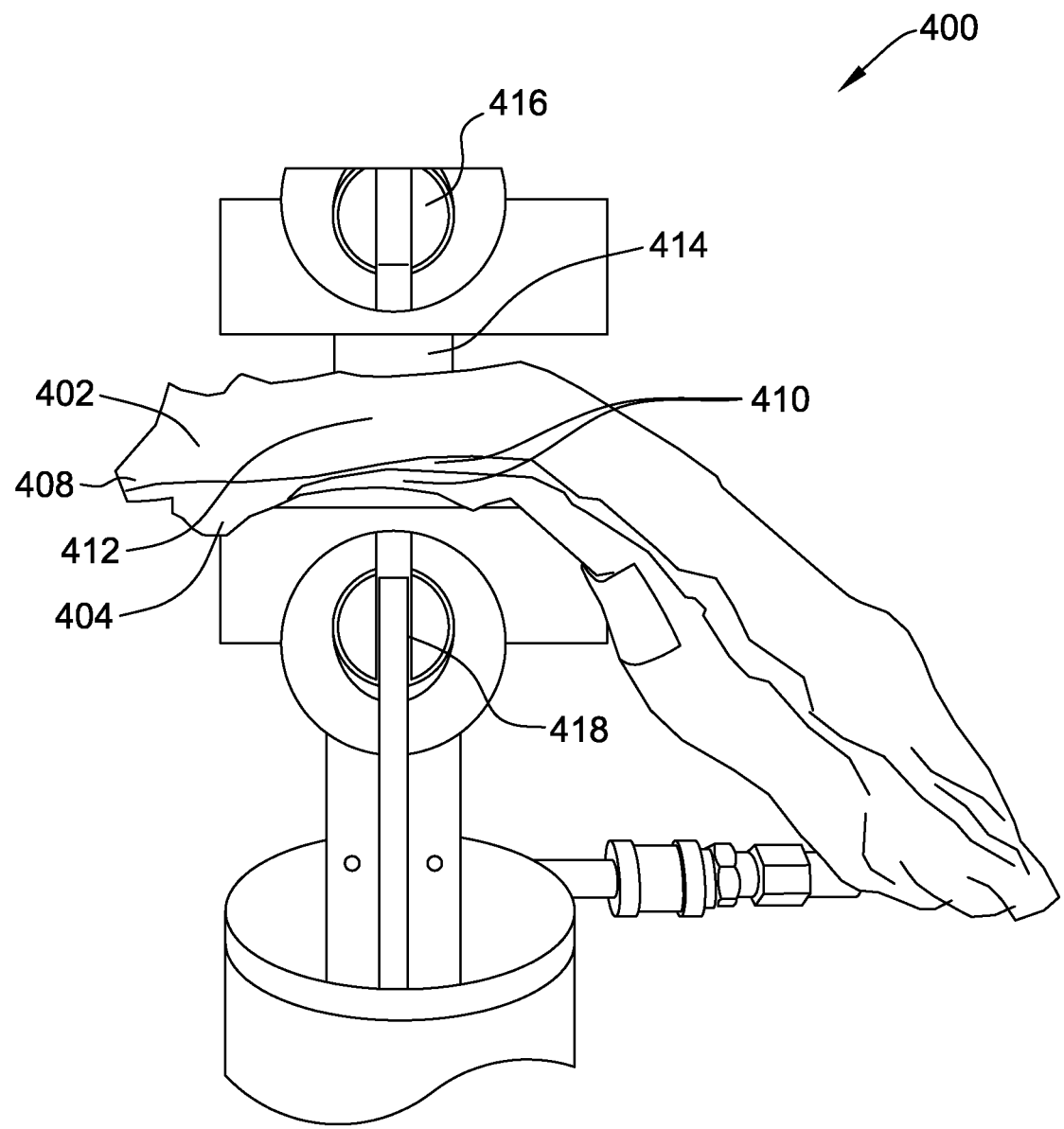
FIG. 18 is a perspective of the folded diaper of FIG. 17 provided in the testing machine according to a Diaper Opening Force Test as described herein.

Turning now to FIGS. 17 and 18, during testing, a test specimen 400 (i.e., the folded diaper 110 or the folded KC-Mexico diaper) was removed from its packaging without unfolding the specimen (e.g., without disengaging the secondary first fastening components 126 from the outer cover 132 of the folded diaper 110). Two pieces of the one inch wide Scotch® 234 masking tape 412 were cut 6.5 inches long. A first of the two pieces of cut masking tape 412 was applied to a front portion 402 of each specimen (i.e., a portion of the folded diaper facing upwards in FIGS. 2 and 10) and a second of the two pieces of masking tape was applied to a back portion 404 of each specimen (i.e., a portion of the folded diaper facing downwards in FIGS. 2 and 10). More specifically, and as best seen in FIG. 17, the first of the two pieces of masking taper 412 was placed on the front portion 402 of the specimen 400 across a lateral length of the specimen at a distance of approximately one inch from a waist edge 408 of the specimen at both longitudinal sides 410 of the specimen and at a distance of approximately 1.25 inches from the waist edge at a center of the specimen.

At the center of the specimen 400, the masking tape 412 was folded into a loop 414 for engagement with an upper jaw 416. More particularly, a 1.25 inch loop 414 was formed at the center of the specimen 400 using the middle 2.5 inches of the masking tape 412. The above procedure was repeated with the second of the two pieces of masking tape 412 such that a second loop 414 was formed and disposed on at a substantially similar position on the back portion 404 of the specimen and configured to engage a lower jaw 418 of the machine.

A distance between the upper jaw 416 and the lower jaw 418 on the machine (i.e., the gauge length) was set at 1.5 inches. Next, the loops 414 provided on the front and back portions 402, 404 were clamped into the upper and lower jaws 416, 418, respectively. Specifically, approximately the outermost 0.75 inch of the loop 414 provided on the front portion 402 of the specimen 400 was clamped into the center of the upper jaw 416, and approximately the outermost 0.75 inch of the loop provided on the bottom side of the specimen was clamped into the center of the lower jaw 418. Each loop 414 was clamped into the respective jaw 416, 418 without breaking the bond between the front and back sides of the specimen (e.g., without disengaging the secondary first fastening component 126 from the outer cover 132) and without disengaging the masking tape 412 from the outer cover of the specimen.

Next, the machine was operated such that the upper jaw 416 traveled upward at a speed of 305 millimeters per minute until the front side of the folded specimen 400 became disengaged from the back side of the folded specimen (e.g., until the secondary first fastening components 126 became disengaged from the outer cover 132). Data was then recorded on a computer for force versus displacement (travel distance of the upper jaw 416) using software called TestWorks® v4.12C provided by MTS System Corporation. The force was recorded to the nearest 0.1 grams-force (gf). The peak load (e.g., the highest force reading) for each tested specimen is thus representative of a typical peel force needed to unfold each tested specimen (e.g., disengage the secondary first fastening components 126 from the outer cover 132).

The above described experiment was performed for a plurality of specimens 400 of the diaper 110 comprising the above described properties for each of the secondary first fastening components 126 and the outer cover 132, as well as a plurality of specimens of the KC-Mexico diaper. The experiment revealed that the peak loads (i.e., a load indicative of a peel force needed to unfold the product) for the KC-Mexico diaper were much higher than the peak loads experienced by the diaper 110 configured as described. More specifically, in the experiment ten specimens of each product were tested with an average peak load of the ten KC-Mexico diapers being 135.5 gf with a standard deviation of 26.1 gf, and an average peak load of the ten diapers according to the disclosure being 91.4 gf with a standard deviation of 13.5 gf. Further, a maximum of the peak loads measured for the KC-Mexico diaper was 176.75 gf, while a maximum of the peak loads measured for the diaper 110 was 116.6 gf.

Table 1 below is the results of the Diaper Opening Force Test for the KC-Mexico diaper and for the product according to the present disclosure.

TABLE 1

KC-Mexico Diaper and present disclosure product
Diaper Opening Force Test results

| Spec. | Peak Load - KC-Mexico (gf) | Peak Load - Embodiment of the disclosure (gf) |
| --- | --- | --- |
| 1 | 176.75 (max) | 80.72 |
| 2 | 122.44 | 106.36 |
| 3 | 173.89 | 87.62 |
| 4 | 166.80 | 94.63 |
| 5 | 118.79 | 70.24 |
| 6 | 124.64 | 89.42 |
| 7 | 117.69 | 90.57 |
| 8 | 108.62 | 79.68 |
| 9 | 117.71 | 116.60 (max) |
| 10 | 176.75 | 97.78 |
| Average Peak Load | 135.50 | 91.36 |
| Standard Deviation | 26.12 | 13.45 |

In some suitable embodiments, the secondary first fastening components 126 may not engage the back waist region (e.g., outer cover 132, ears 122, etc.) with any force. For example, in some embodiments (and as discussed) the secondary first fastening components 126 may comprise one or more loop fasteners, and the secondary second fastening components 178 may comprise hook fasteners. In such embodiments, the hook fasteners of the secondary second fastening components 178 may be folded over before the diaper 110 is folded along the lateral fold line 144 (as discussed in connection with the various folding processes described above). Accordingly, when the diaper 110 is ultimately folded along lateral fold line 144, the loop fasteners of the secondary first fastening components may engage the back waist portion with little or no force. In such embodiments, the Diaper Opening Test would indicate a very small peak force or even a zero peak force is needed to unfold the diaper.

Figure 19:
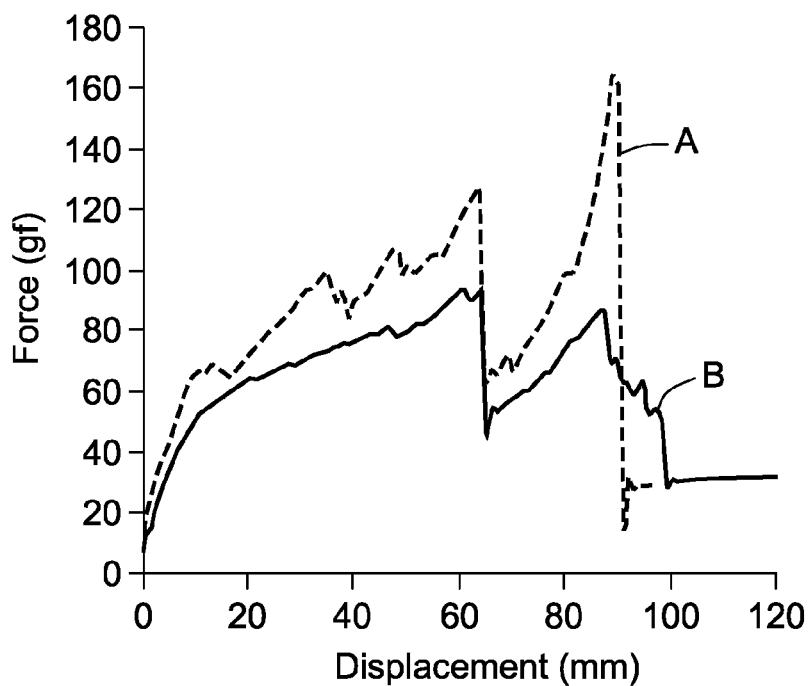
FIG. 19 is a plot of force v. displacement for a specimen of a prior art product and a specimen of one embodiment of the present disclosure product according to the Diaper Opening Force Test.

FIG. 19 illustrates a plot of force vs. displacement for one example of the Diaper Opening Force Test discussed above. Two trend lines are plotted in the diagram, each trend line showing the amount of force exerted on the specimen versus displacement (travel distance of the upper jaw 416). Trend line A indicates the amount of force versus displacement for the KC-Mexico product, and trend line B indicates the amount of force versus displacement for a product according to aspects of this disclosure. The peak force of each trend line is generally indicative of an amount of force needed to disengage, e.g., the secondary first fastening components 126 from the outer cover 132. As easily seen in FIG. 19, and as discussed above, the amount of force needed to disengage the fasteners provided on the KC-Mexico diaper from its outer cover was much higher than the amount of force needed to disengage the secondary first fastening components 126 from the outer cover 132 on the product according to the present disclosure.

Accordingly, because the KC-Mexico diaper experienced much higher peak loads before the pair of fasteners came disengaged from the outer cover than the peak loads required to disengage the secondary first fastening components 126 from the outer cover 132 of the diaper 110, the KC-Mexico diaper thus requires much more force to unfold the product than does the diaper according to aspects of this disclosure. Accordingly, a user of the diaper 110 may more readily unfold the diaper 110 during use without, e.g., risking tearing or delaminating the outer cover 132 of the diaper.

Figure 20:
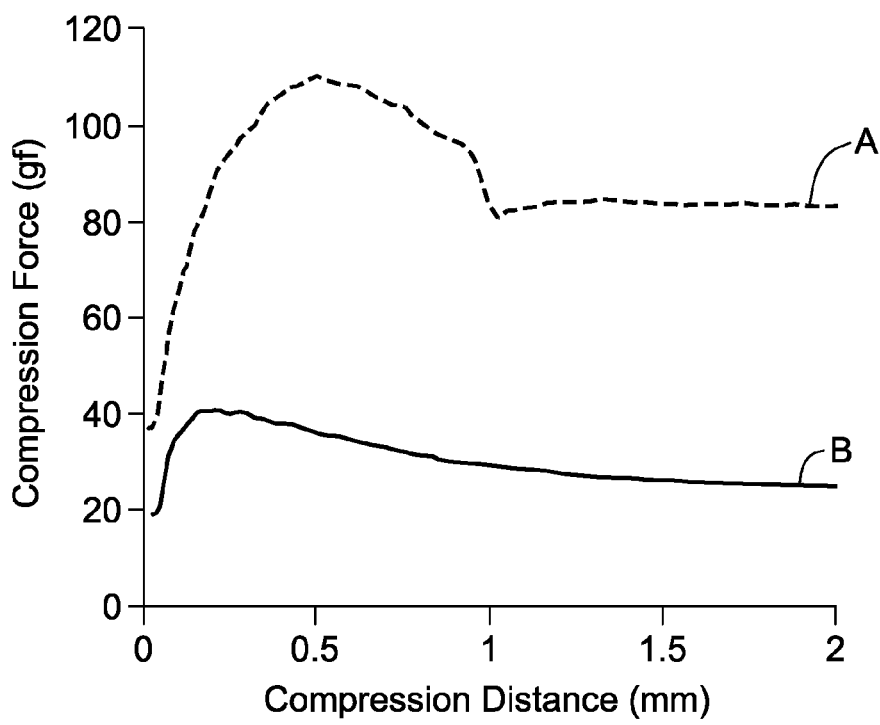
FIG. 20 is a plot of compression force vs. compression distance for a specimen of a prior art product and a specimen of one embodiment of the present disclosure product according to an Edge Stiffness Test as described herein.

FIG. 20 illustrates a plot of compression force vs. compression distance for one example of an Edge Stiffness Test. Two trend lines are plotted in the diagram, each trend line showing the amount of force needed to bend or buckle a specimen upon applying a force to the edge of the specimen. For instance, trend line B indicates that the compression force required to bend or buckle the specimen from a product made in accordance with the present disclosure increased until the specimen buckled at a peak compression force of 40.6 grams-force (after only a slight amount of compression distance). After the peak compression load, the compression force required to further bend the specimen decreased asymptotically towards approximately 20 grams-force.

Continuing with FIG. 20, trend line A indicates that the compression force required to bend or buckle the specimen from the KC-Mexico diaper increases until the specimen buckled at a peak compression force of 110.7 grams-force. After the peak compression load, the compression force required to further bend the specimen decreased asymptotically towards approximately 80 grams-force. Further and more detailed discussion of FIG. 20 can be found in the Edge Stiffness Test section hereinbelow.

In one embodiment, the secondary first fastening components 126 (i.e., the hook fasteners of the illustrated embodiment) on the front portion 116 of the diaper 110 each have a relatively low stiffness at least in the longitudinal direction 112 of the diaper to facilitate decreased red marking of and discomfort to the wearer of the diaper. As used herein, the stiffness of the secondary first fastening components 126 refers generally to the resistance of each component to deflection or deformation (e.g., bending) when acted on by an applied force. For example, in one suitable embodiment, the stiffness may be a Gurley stiffness as determined in a Gurley Stiffness Test. In other embodiments the stiffness may be an edge stiffness as determined in an Edge Stiffness Test.

Gurley Stiffness Test

A Gurley Stiffness Test is commonly used to determine the stiffness of a test specimen (such as, e.g., the secondary first fastening component 126) with respect to a bending moment produced by a force that is directed perpendicular to the plane substantially defined by the length and width of the specimen being tested. A description of a Gurley Stiffness Test is set forth in TAPPI Standard Test T543 om-94 (Bending Resistance of Paper (Gurley type tester). One suitable testing apparatus for conducting the Gurley Stiffness Test is a Gurley Digital Stiffness Tester, Model 31644 manufactured by Teledyne Gurley, a business having offices in Troy, N.Y.

For purposes of the present disclosure, the stated Gurley stiffness values are those that would be generated by a standard sized sample (i.e., 1 inch wide by 3.5 inches long) using the Gurley Digital Stiffness Tester. Accordingly, the readings from the Tester are appropriately converted to the stiffness of a standard sized sample (i.e., 1 inch wide by 3.5 inches long), and are reported in terms of milligrams (mg) of force.

In general, the Gurley Digital Stiffness Tester consists of a pendulum with slots for attaching various weights. The specimen to be tested presses the pendulum to the right and to the left resulting in two readings. The readings are positively correlated with a specimen's stiffness. The two readings are then averaged and multiplied by a factor. This factor is determined by the specimen size, the distance from the center pivot, and the weight used on the pendulum. Methodology of the Gurley Stiffness Test is set forth below.

For purposes of the present disclosure, test specimens are prepared, e.g., taken from a larger sample or product, by cutting the specimen to have its length in the longitudinal or machine direction of the product. As an example, for the present disclosure where the secondary first fastening components (e.g., hook fasteners) are being tested, the specimens are cut from the diaper to include the fastener along with the material to which it is attached, e.g., the outer cover of the diaper. Each specimen should be cut to 12 mm wide by 25 mm long±1 mm (or 0.5 inches by 1 inch±0.04 inches).

To conduct the Gurley Stiffness Test using the Gurley Digital Stiffness Tester, the base of the instrument is first leveled by adjusting the leveling screw until the level's bubble is centered and the pendulum's pointer indicates zero. After turning the power on, the specimen is used to determine the appropriate weight and the weight position on the pendulum to obtain a reading between 2 and 6 on the scale/display. The switches are set to correspond to the weight being used, the weight's position on the pendulum, the width of the specimen being tested, and the length of the specimen.

For each specimen, the specimen strip is centered over the pendulum such that 6.4 mm±1 mm (or 0.25 inches±0.04 inches) overlaps the top of the pendulum and 6.4 mm±1 mm (or 0.25 inches±0.04 inches) is held in the jaws of the Tester. The system is reset so that the display reads 00-000-00. The Motor-Direction switch is operated to engage the clamp arm to press the specimen against the pendulum. Both a left reading and a right reading are taken, and an average reading is determined. The SELECT button on the Tester is then pressed to obtain the stiffness (in milligrams) calculation and the stiffness is recorded. The aforementioned steps are repeated for each test specimen in the sample group.

Example

Secondary first fastening components from two different absorbent products were subjected to the Gurley Stiffness Test to assess the relative Gurley stiffness of each. The first product was the KC-Mexico diaper, which has fastening components being hook fasteners and being made of polypropylene. Each specimen had the following test conditions: weight 25 g, and weight position 4"; and measurements: width 0.5", and length 1". The second product was made in accordance with the present disclosure with the fastening components being hook fasteners and being made of polyethylene. Each specimen had the following test conditions: weight 25 g, and weight position 2"; and measurements: width 0.5", and length 1". Ten specimens of each product were tested. As used herein when referring to the Gurley Stiffness test, "length" generally refers to a direction in the longitudinal direction of the product, and "width" generally refers to a dimension in the lateral direction of the product. Further, "weight" and "weight position" generally refer to test conditions which indicate how much force is attached to the pendulum and at what position during the test.

Table 2 below is the results of the Gurley Stiffness Test for the KC-Mexico diaper and Table 3 is the results for the product according to the present disclosure.

TABLE 2

KC-Mexico Diaper Gurley Stiffness Test results

| Spec. | Right | Left | Ave. | Stiffness (mg) |
|---|---|---|---|---|
| 1 | 3.30 | 4.80 | 4.05 | 225.18 |
| 2 | 2.50 | 4.60 | 3.55 | 197.38 |
| 3 | 3.00 | 4.60 | 3.80 | 211.28 |
| 4 | 2.60 | 4.10 | 3.35 | 186.26 |
| 5 | 3.00 | 4.40 | 3.70 | 205.72 |
| 6 | 2.90 | 3.80 | 3.35 | 186.26 |
| 7 | 2.10 | 4.70 | 3.40 | 189.04 |
| 8 | 3.70 | 4.10 | 3.90 | 216.84 |
| 9 | 3.10 | 5.70 | 4.40 | 244.64 |
| 10 | 2.70 | 5.10 | 3.90 | 216.84 |
| Ave. | 2.89 | 4.59 | 3.74 | 207.94 |
| Std. | 0.45 | 0.55 | 0.34 | 18.94 |

TABLE 3

Present disclosure product Gurley Stiffness Test results

| Spec. | Right | Left | Ave. | Stiffness (mg) |
|---|---|---|---|---|
| 1 | 1.40 | 2.80 | 2.10 | 116.76 |
| 2 | 1.70 | 3.70 | 2.70 | 150.12 |
| 3 | 1.90 | 2.90 | 2.40 | 130.44 |
| 4 | 1.50 | 3.00 | 2.25 | 125.10 |
| 5 | 1.60 | 2.70 | 2.15 | 119.54 |
| 6 | 1.90 | 4.40 | 3.15 | 175.14 |
| 7 | 1.70 | 2.70 | 2.20 | 122.32 |
| 8 | 1.70 | 2.70 | 2.20 | 122.32 |
| 9 | 1.30 | 3.10 | 2.20 | 122.32 |
| 10 | 2.00 | 4.50 | 3.25 | 180.70 |
| Ave. | 1.67 | 3.25 | 2.46 | 136.48 |
| Std. | 0.23 | 0.70 | 0.43 | 23.76 |

The tested fastening components from the KC-Mexico diaper had an average stiffness of 207.94 mg whereas the tested fastening components from the present disclosure product had an average stiffness of 136.48 mg. Additionally, the tested fastening components from the KC-Mexico diaper ranged from a minimum stiffness of 186.26 mg to a maximum stiffness of 244.64 mg. The tested fastening components from the present disclosure product ranged from a minimum stiffness of 116.76 mg to a maximum stiffness of 180.70 mg. In other words, the minimum stiffness (186.26 mg) of the tested components of the KC-Mexico diaper was greater than the maximum stiffness (180.70 mg) of the tested fastening components from the present disclosure product. Put differently, every tested fastening component from the present disclosure product had a Gurley stiffness of less than 185 mg.

To this end, in one embodiment the secondary first fastening component 126, and more particularly the secondary hook fastener on the front portion 116 of the diaper 110 as in the illustrated embodiment, has a Gurley stiffness according to the Gurley Stiffness Test of less than 185 mg, more suitably less than 170 mg, even more suitably less than 160 mg, still more suitably less than 150 mg, and still more suitably less than 140 mg. In another embodiment the secondary first fastening component 126, and more particularly the secondary hook fastener on the front portion 116 of the diaper 110 as in the illustrated embodiment, has an average Gurley stiffness according to the Gurley Stiffness Test of less than 180 mg for a sample size of at least 10 specimens, more suitably less than 170 mg, even more suitably less than 160 mg, still more suitably less than 150 mg, and still more suitably less than 140 mg. It is understood that in other embodiments the Gurley stiffness, and/or the average Gurley stiffness of the secondary first fastening component 126 may be even less than the ranges set forth above and remain within the scope of the disclosure.

Edge Stiffness Test

An Edge Stiffness Test determines the edge stiffness of a test specimen 500 (such as, e.g., the secondary first fastening component 126), and more particularly it measures the amount of force, in grams (grams-force, or gf), required to buckle or bend upon applying a longitudinal force against an edge of the specimen. This is indicative, for example, of the manner in which a force would be applied by a wearer to the secondary first fastening components 126 of the diaper 110 when the wearer bends over at the waist.

Figure 21:
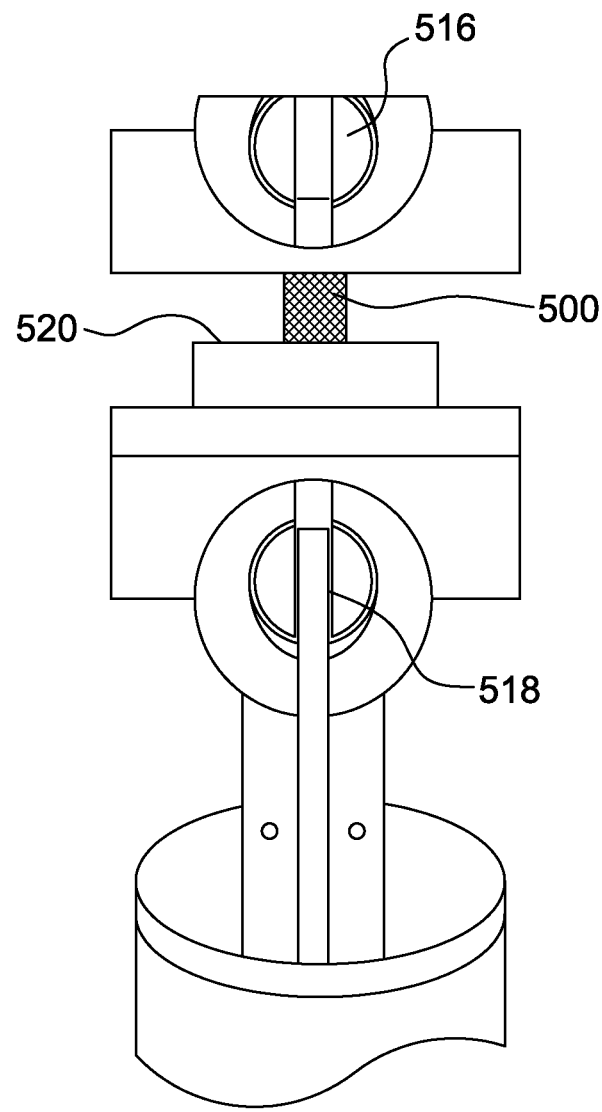
FIG. 21 is a perspective of a test specimen provided in a testing machine according to the Edge Stiffness Test.

Turning now to FIG. 21, a rectangular (elongate) specimen 500 is held upright (i.e., lengthwise) by a grip, or jaws (i.e., upper jaw 516 and lower jaw 518), with the short edge or end of the specimen perpendicular to and in contact with a flat surface or platen 520. The contact edge is then gradually urged against the flat surface by moving the grip or jaws 516, 518 toward the flat surface 520 by a recorded distance until the specimen buckles or bends. As can be seen from FIG. 20, which is a plot of compression force versus compression distance (i.e., the distance that the grip or jaws 516, 518 move toward the flat surface during testing) and is described in further detail later herein, the compression force initially increases proportionately with compressed distance, i.e., the distance that the grip or jaws move toward the flat surface 520. After reaching a peak compression force, the force decreases asymptotically toward a constant while the compressed distance increases. The edge stiffness is the peak compression force achieved during the test, with a lower compression force meaning that the specimen 500 has a lower edge stiffness, or is more easily bent upon application of a force to the edge of the specimen.

One suitable testing apparatus for conducting the Edge Stiffness Test is an MTS Sintech tensile frame 500S manufactured by MTS System Corporation, a business having offices in Eden Prairie, Minn. Additional instruments used to conduct the Edge Stiffness Test include a load cell 100 Newton D86201, an upper fixture having a upper jaw 516 measuring 1" long and 3" wide, and a low fixture stainless steel platen 520 having a diameter measuring 3.5" (all manufactured by MTS System Corporation). Also used is a thickness measurement device such as a Sony Digital Indicator U30A equipped with a 0.05 psi platen, manufactured by Sony Corporation of America, a business having offices in New York, N.Y.

To conduct the Edge Stiffness Test for the purposes of the present disclosure, specimens 500 are cut to have a width of 15 mm in the lateral direction 114 of the product, such as the diaper 110 of the illustrated embodiment, and a length of 40 mm in the longitudinal direction 112 of the product. The thickness of each specimen 500 is measured using the thickness measurement device with a 0.05 psi platen to the nearest 0.001 mm. The distance between the lower platen 520 and the bottom of the upper jaw 516 is set at 10 mm and the specimen 500 is placed in the upper jaw with the specimen oriented lengthwise. The lower edge of the specimen 500 is in slight contact with the flat surface of the lower platen 520.

The upper jaw 516 is activated to move downward toward the lower platen 520 at a speed of 6.35 mm/min. (0.25 inches/min.) to longitudinally compress the specimen 500 until the force drops from the peak and levels off. Test data of the compression force vs. compression distance (e.g., downward travel distance of the upper jaw 516) is recorded on a PC using software having the trade name TestWorks V4.12C provided by MTS System Corporation. The compression force is reported to the nearest 0.1 grams-force (gf). The peak compression load (in gf) for each specimen 500 tested is determined using this software. The peak compression stress in gf/mm² is calculated by dividing the peak compression load in gf by the cross sectional area in mm².

Example

Secondary first fastening components from two different absorbent products were subjected to the Edge Stiffness Test to assess the relative edge stiffness of each. The first product was the KC-Mexico diaper having hook fasteners made of polypropylene. The second product was a diaper 110 made in accordance with the present disclosure with the secondary first fastening components 126 being hook fasteners and being made of polyethylene. Five specimens 500 of each product were tested.

Table 4 below is the results of the Edge Stiffness Test for the KC-Mexico diaper and Table 5 is the results for the product according to the present disclosure. The Peak Load is the edge stiffness, in grams-force (gf).

TABLE 4

KC-Mexico Diaper Edge Stiffness Test results

| Spec. | Thickness (mm) | Width (mm) | Peak Load (gf) | Peak Stress (gf/mm²) |
| --- | --- | --- | --- | --- |
| 1 | 0.728 | 15 | 115 | 10.5 |
| 2 | 0.72 | 15 | 158.2 | 14.6 |
| 3 | 0.761 | 15 | 100.1 | 8.8 |
| 4 | 0.768 | 15 | 149.5 | 13.0 |
| 5 | 0.689 | 15 | 110.7 | 10.7 |
| Ave | 0.733 | 15 | 126.7 | 11.5 |
| Std | 0.032 | 0 | 25.6 | 2.3 |

TABLE 5

Present disclosure product Edge Stiffness Test results

| Spec. | Thickness (mm) | Width (mm) | Peak Load (gf) | Peak Stress (gf/mm²) |
| --- | --- | --- | --- | --- |
| 1 | 0.651 | 15 | 68.2 | 7.0 |
| 2 | 0.772 | 15 | 38.5 | 3.3 |
| 3 | 0.735 | 15 | 43.7 | 4.0 |
| 4 | 0.768 | 15 | 53.4 | 4.6 |
| 5 | 0.739 | 15 | 40.6 | 3.7 |
| Ave | 0.733 | 15 | 48.9 | 4.5 |
| Std | 0.049 | 0 | 12.2 | 1.5 |

FIG. 20 is a plot of compression force vs. compression distance for specimen #5 of the KC-Mexico diaper (trend line A) and specimen #5 of the present disclosure product (trend line B) of the above Edge Stiffness Test. Each curve shows the amount of force needed to bend or buckle the specimen upon applying a force to the edge of the specimen. For instance, trend line B indicates that the compression force required to bend or buckle the specimen from a product made in accordance with the present disclosure increased until the specimen buckled at a peak compression force of 40.6 grams-force (after only a slight amount of compression distance). After the peak compression load, the compression force required to further bend the specimen 500 decreased asymptotically towards approximately 20 grams-force.

Trend line A indicates that the compression force required to bend or buckle the specimen 500 from the KC-Mexico diaper increases until the specimen buckled at a peak compression force of 110.7 grams-force. After the peak compression load, the compression force required to further bend the specimen 500 decreased asymptotically towards approximately 80 grams-force. Accordingly, it required more force to compress the edge of a specimen 500 from the KC-Mexico diaper than it did to compress the edge of a specimen from a product made according to present disclosure. Therefore, it can be concluded that the edge stiffness of the secondary first fastening component 126 of the present disclosure product was less stiff than that of the KC-Mexico diaper.

Accordingly, in one embodiment the secondary first fastening component 126, and more particularly the secondary hook fastener on the front portion 116 of the diaper 110 as in the illustrated embodiment, has an edge stiffness according to the Edge Stiffness Test of less than 100 grams-force, more suitably less than 90 grams-force, even more suitably less than 80 grams-force, still more suitably less than 70 grams-force, and still more suitably less than 60 grams-force. In other embodiments it is less than 50 grams-force.

In another embodiment the secondary first fastening component 126, and more particularly the secondary hook fastener on the front portion 116 of the diaper 110 as in the illustrated embodiment, has an average edge stiffness according to the Edge Stiffness Test of less than 80 grams-force for a sample size of at least 5 specimens, more suitably less than 70 grams-force, even more suitably less than 60 grams-force, and still more suitably less than 50 grams-force. It is understood that in other embodiments the edge stiffness and/or the average edge stiffness of the secondary first fastening component 126 may be even less than the ranges set forth above and remain within the scope of the disclosure.

With reference to Tables 4 and 5, the KC-Mexico diaper specimens 500 had an average peak load of 126.7 grams-force whereas the present disclosure specimens had an average peak load of 48.9 grams-force. Another embodiment of the present disclosure has an average peak load of less than 90 grams-force based on a sample size of at least 5 samples. Another embodiment of the present disclosure with a sample size of at least 5 samples has an average peak load of less than 80 grams-force. Yet another embodiment of the present disclosure with a sample size of at least 5 samples has an average peak load of less than 70 grams-force. Yet another embodiment of the present disclosure with a sample size of at least 5 samples has an average peak load of less than 60 grams-force.

With continued reference to Tables 4 and 5, the KC-Mexico diaper specimens 500 shown in Table 4 ranged from a minimum peak load of 100.1 grams-force to a maximum peak load of 158.2 grams-force. The present disclosure specimens 500 shown in Table 5 ranged from a minimum peak load of 38.5 grams-force to a maximum peak load of 68.2 grams-force. In other words, every specimen 500 in the present disclosure sample had a peak load of less than 100 grams-force.

Thus, in view of either one of the Gurley Stiffness Test and the Edge Stiffness Test, particularly as used in the above Examples, it is evident that the secondary first fastening components 126 are less stiff than the secondary first fastening components of the KC-Mexico diaper. As used on the diaper 110 described herein, such a reduced stiffness increases comfort for the wearer and reduces red marks that may irritate the skin.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article having an inner surface, an outer surface, a front waist portion, a back waist portion, a crotch portion extending longitudinally between and connecting the front waist portion and the back waist portion, the absorbent article comprising:
   a chassis having longitudinally opposite ends, transversely opposite sides defining respective side edges, a bodyside liner at least in part defining the inner surface of the article, an outer cover at least in part defining the outer surface of the article, and an absorbent core disposed between the liner and the outer cover;
   a pair of ears extending transversely outward from the opposite sides of the chassis at the back waist portion thereof; and
   a fastening system comprising a primary fastening system and a secondary fastening system, the primary fastening system comprising a primary first fastening component disposed on each of the pair of ears and a primary second fastening component disposed on the outer surface of the article at the front waist portion, the secondary fastening system comprising a secondary second fastening component on each of the pair of ears and a corresponding pair of spaced apart secondary first fastening components on the outer surface of the article at the front waist portion, each of the secondary first fastening components having a transversely inboard-most longitudinal edge that is disposed transversely inward of a transversely inboard-most point of the respective side edges and having a stiffness in the longitudinal direction of the article of less than 185 milligrams according to a Gurley Stiffness Test;
   wherein the absorbent article includes a pair of longitudinally extending foldlines disposed in the front waist portion, and wherein the inboard-most longitudinal edge of each of the secondary first fastening components is transversely outward and spaced apart from a respective longitudinally extending foldline at least a distance equal to a predetermined process range.

2. The absorbent article set forth in claim 1 wherein the secondary first fastening component has the stiffness in the longitudinal direction of the article of less than 160 milligrams according to the Gurley Stiffness Test.

3. The absorbent article set forth in claim 1 wherein the secondary first fastening component has an average stiffness in the longitudinal direction of the article of less than 180 milligrams according to the Gurley Stiffness Test based on a sample size of at least 10 samples.

4. The absorbent article set forth in claim 3 wherein the secondary first fastening component has the average stiffness in the longitudinal direction of the article of less than 160 milligrams according to the Gurley Stiffness Test based on the sample size of at least 10 samples.

5. The absorbent article set forth in claim 4 wherein the secondary first fastening component has the average stiffness in the longitudinal direction of the article of less than 140 milligrams according to the Gurley Stiffness Test based on the sample size of at least 10 samples.

6. The absorbent article set forth in claim 1 wherein the secondary first fastening component is disposed transversely adjacent to the primary second fastening component.

7. The absorbent article set forth in claim 1 wherein the secondary first fastening component is disposed on the primary second fastening component.

8. The absorbent article set forth in claim 1 wherein the primary first fastening component comprises a hook fastener and the primary second fastening component comprises a loop fastener.

9. The absorbent article set forth in claim 1 wherein the chassis has a width at the front waist portion of the article and the absorbent core has a width at the front waist portion of the article that is less than the width of the chassis at said front waist portion of the article, the secondary first fastening component being disposed on the outer surface of the article at the front waist portion thereof transversely between an inboard-most portion of the absorbent core and a respective side of the chassis at the front waist portion of the article.

10. The absorbent article set forth in claim 1 wherein the secondary second fastening components each comprise a loop fastener and the secondary first fastening components each comprise a hook fastener.

11. An absorbent article having an inner surface, an outer surface, a first waist portion, a second waist portion, a crotch portion extending longitudinally between and connecting the first waist portion and the second waist portion, the absorbent article comprising:
    a chassis having longitudinally opposite ends, transversely opposite sides defining respective side edges, a bodyside liner at least in part defining the inner surface of the article, an outer cover at least in part defining the outer surface of the article, and an absorbent core disposed between the liner and the outer cover;
    a pair of ears extending transversely outward from the opposite sides of the chassis at the second waist portion thereof; and
    a fastening system comprising a primary fastening system and a secondary fastening system, the primary fastening system comprising a primary first fastening component disposed on each of the pair of ears and a primary second fastening component disposed on the outer surface of the article at the first waist portion, the secondary fastening system comprising a secondary second fastening component on each of the pair of ears and a corresponding pair of spaced apart secondary first fastening components on the outer surface of the article at the first waist portion, each of the secondary first fastening components having a transversely inboard-most longitudinal edge that is disposed transversely inward of a transversely inboard-most point of the respective side edges and having a peak load corresponding to an edge stiffness in the longitudinal direction of the article of less than 100 grams-force according to an Edge Stiffness Test;
    wherein the absorbent article includes a pair of longitudinally extending foldlines disposed in the first waist portion, and wherein the inboard-most longitudinal edge of each of the secondary first fastening components is transversely outward and spaced apart from a respective longitudinally extending foldline at least a distance equal to a predetermined process range.

12. The absorbent article set forth in claim 11 wherein the secondary first fastening component has the peak load corresponding to the edge stiffness in the longitudinal direction of the article of less than 80 grams-force according to the Edge Stiffness Test.

13. The absorbent article set forth in claim 11 wherein the secondary first fastening component has an average peak load corresponding to the edge stiffness in the longitudinal direction of the article of less than 90 grams-force according to the Edge Stiffness Test based on a sample size of at least 5 samples.

14. The absorbent article set forth in claim 13 wherein the secondary first fastening component has the average peak load corresponding to the edge stiffness in the longitudinal direction of the article of less than 80 grams-force according to the Edge Stiffness Test based on the sample size of at least 5 samples.

15. The absorbent article set forth in claim 14 wherein the secondary first fastening component has the average peak load corresponding to the edge stiffness in the longitudinal direction of the article of less than 60 grams-force according to the Edge Stiffness Test based on the sample size of at least 5 samples.

16. The absorbent article set forth in claim 11 wherein the secondary first fastening component is disposed transversely adjacent to the primary second fastening component.

17. The absorbent article set forth in claim 11 wherein the secondary first fastening component is disposed on the primary second fastening component.

18. The absorbent article set forth in claim 11 wherein the primary first fastening component comprises a hook fastener and the primary second fastening component comprises a loop fastener.

19. The absorbent article set forth in claim 11 wherein the chassis has a width at the first waist portion of the article and the absorbent core has a width at the first waist portion of the article that is less than the width of the chassis at said first waist portion of the article, the secondary first fastening component being disposed on the outer surface of the article at the first waist portion thereof transversely between an inboard-most portion of the absorbent core and a respective side of the chassis at the first waist portion of the article.

20. The absorbent article set forth in claim 11 wherein the secondary second fastening components each comprise a loop fastener and the secondary first fastening components each comprise a hook fastener.

21. An absorbent article having an inner surface, an outer surface, a first waist portion, a second waist portion, a crotch portion extending longitudinally between and connecting the first waist portion and the second waist portion, the absorbent article comprising:
a chassis having longitudinally opposite ends, transversely opposite sides defining respective side edges, a bodyside liner at least in part defining the inner surface of the article, an outer cover at least in part defining the outer surface of the article, and an absorbent core disposed between the liner and the outer cover;
a pair of ears extending transversely outward from the opposite sides of the chassis at the second waist portion thereof; and
a fastening system comprising a primary fastening system and a secondary fastening system, the primary fastening system comprising a primary first fastening component disposed on each of the pair of ears and a primary second fastening component disposed on the outer surface of the article at the first waist portion, the secondary fastening system comprising a secondary second fastening component on each of the pair of ears and a corresponding pair of spaced apart secondary first fastening components on the outer surface of the article at the first waist portion, each of the secondary first fastening component having a transversely inboard-most longitudinal edge that is disposed transversely inward of a transversely inboard-most point of the respective side edges and having a peak stress corresponding to an edge stiffness in the longitudinal direction of the article of less than 8.5 grams-force per square millimeter according to an Edge Stiffness Test;
wherein the absorbent article includes a pair of longitudinally extending foldlines disposed in the first waist portion, and wherein the inboard-most longitudinal edge of each of the secondary first fastening components is transversely outward and spaced apart from a respective longitudinally extending foldline at least a distance equal to a predetermined process range.

22. The absorbent article set forth in claim 21 wherein the secondary first fastening component has the peak stress corresponding to the edge stiffness in the longitudinal direction of the article of less than 7.5 grams-force per square millimeter according to the Edge Stiffness Test.

23. The absorbent article set forth in claim 21 wherein the secondary first fastening component has an average peak stress corresponding to the edge stiffness in the longitudinal direction of the article of less than 9.0 grams-force per square millimeter according to the Edge Stiffness Test based on a sample size of at least 5 samples.

24. The absorbent article set forth in claim 23 wherein the secondary first fastening component has the average peak stress corresponding to the edge stiffness in the longitudinal direction of the article of less than 7.5 grams-force per square millimeter according to the Edge Stiffness Test based on the sample size of at least 5 samples.

25. The absorbent article set forth in claim 24 wherein the secondary first fastening component has the average peak stress corresponding to the edge stiffness in the longitudinal direction of the article of less than 5.0 grams-force per square millimeter according to the Edge Stiffness Test based on the sample size of at least 5 samples.

26. The absorbent article set forth in claim 21 wherein the secondary first fastening component is disposed transversely adjacent to the primary second fastening component.

27. The absorbent article set forth in claim 21 wherein the secondary first fastening component is disposed on the primary second fastening component.

28. The absorbent article set forth in claim 21 wherein the primary first fastening component comprises a hook fastener and the primary second fastening component comprises a loop fastener.

29. The absorbent article set forth in claim 21 wherein the chassis has a width at the first waist portion of the article and the absorbent core has a width at the first waist portion of the article that is less than the width of the chassis at said first waist portion of the article, the secondary first fastening component being disposed on the outer surface of the article at the first waist portion thereof transversely between an inboard-most portion of the absorbent core and a respective side of the chassis at the first waist portion of the article.

30. The absorbent article set forth in claim 21 wherein the secondary second fastening components each comprise a loop fastener and the secondary first fastening components each comprise a hook fastener.

31. An absorbent article having an inner surface, an outer surface, a first waist portion, a second waist portion, a crotch portion extending longitudinally between and connecting the first waist portion and the second waist portion, the absorbent article comprising:

a chassis having longitudinally opposite ends, transversely opposite sides defining respective side edges, a bodyside liner at least in part defining the inner surface of the article, an outer cover at least in part defining the outer surface of the article, and an absorbent core disposed between the liner and the outer cover;

a pair of ears secured to and extending transversely outward from the opposite sides of the chassis at the second waist portion thereof; and a fastening system comprising a primary fastening system and a secondary fastening system, the primary fastening system comprising a primary first fastening component disposed on each of the pair of ears and a primary second fastening component disposed on the outer surface of the article at the first waist portion, the secondary fastening system comprising a secondary second fastening component on each of the pair of ears and a corresponding pair of spaced apart secondary first fastening components on the outer surface of the article at the first waist portion, each of the secondary first fastening components having a transversely inboard-most longitudinal edge that is disposed transversely inward of a transversely inboard-most point of the respective side edges and having a Gurley stiffness in the longitudinal direction of the article of less than 185 milligrams according to a Gurley Stiffness Test, the secondary first fastening component further having a peak load corresponding to an edge stiffness in the longitudinal direction of the article of less than 100 grams-force according to an Edge Stiffness Test;

wherein the absorbent article includes a pair of longitudinally extending foldlines disposed in the first waist portion, and wherein the inboard-most longitudinal edge of each of the secondary first fastening components is transversely outward and spaced apart from a respective longitudinally extending foldline at least a distance equal to a predetermined process range.

32. The absorbent article set forth in claim 31 wherein the secondary first fastening component has the stiffness in the longitudinal direction of the article of less than 160 milligrams according to the Gurley Stiffness Test.

33. The absorbent article set forth in claim 31 wherein the secondary first fastening component has an average stiffness in the longitudinal direction of the article of less than 180 milligrams according to the Gurley Stiffness Test based on a sample size of at least 10 samples.

34. The absorbent article set forth in claim 33 wherein the secondary first fastening component has the average stiffness in the longitudinal direction of the article of less than 160 milligrams according to the Gurley Stiffness Test based on the sample size of at least 10 samples.

35. The absorbent article set forth in claim 34 wherein the secondary first fastening component has the average stiffness in the longitudinal direction of the article of less than 140 milligrams according to the Gurley Stiffness Test based on the sample size of at least 10 samples.

36. The absorbent article set forth in claim 31 wherein the secondary first fastening component has the peak load corresponding to the edge stiffness in the longitudinal direction of the article of less than 80 grams-force according to the Edge Stiffness Test.

37. The absorbent article set forth in claim 31 wherein the secondary first fastening component has an average peak load corresponding to the edge stiffness in the longitudinal direction of the article of less than 90 grams-force according to the Edge Stiffness Test based on a sample size of at least 5 samples.

38. The absorbent article set forth in claim 37 wherein the secondary first fastening component has the average peak load corresponding to the edge stiffness in the longitudinal direction of the article of less than 80 grams-force according to the Edge Stiffness Test based on the sample size of at least 5 samples.

* * * * *